United States Patent
Seelig et al.

(10) Patent No.: US 12,305,221 B2
(45) Date of Patent: *May 20, 2025

(54) METHODS AND KITS FOR LABELING CELLULAR MOLECULES

(71) Applicant: University of Washington, Seattle, WA (US)

(72) Inventors: Georg Seelig, Seattle, WA (US); Richard Muscat, London (GB); Alexander B. Rosenberg, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/887,088

(22) Filed: Sep. 17, 2024

(65) Prior Publication Data
US 2025/0011837 A1    Jan. 9, 2025

Related U.S. Application Data

(63) Continuation of application No. 18/650,305, filed on Apr. 30, 2024, now Pat. No. 12,252,735, which is a continuation of application No. 18/536,654, filed on Dec. 12, 2023, now Pat. No. 11,987,838, which is a continuation of application No. 17/814,771, filed on Jul. 25, 2022, now Pat. No. 12,195,786, which is a continuation of application No. 17/695,671, filed on Mar. 15, 2022, now Pat. No. 11,555,216, which is a continuation of application No. 17/521,263, filed on Nov. 8, 2021, now Pat. No. 11,427,856, which is a continuation of application No. 17/249,257, filed on Feb. 25, 2021, now Pat. No. 11,168,355, which is a continuation of application No. 17/122,321, filed on Dec. 15, 2020, now Pat. No. 11,634,751, which is a continuation of application No. 14/941,433, filed on Nov. 13, 2015, now Pat. No. 10,900,065.

(60) Provisional application No. 62/080,055, filed on Nov. 14, 2014.

(51) Int. Cl.
*C12Q 1/6806* (2018.01)
*C12N 15/10* (2006.01)
*C12Q 1/6855* (2018.01)

(52) U.S. Cl.
CPC ....... *C12Q 1/6806* (2013.01); *C12N 15/1065* (2013.01); *C12Q 1/6855* (2013.01)

(58) Field of Classification Search
None
See application file for complete search history.

(56) References Cited

U.S. PATENT DOCUMENTS

| | | |
|---|---|---|
| 5,962,272 A | 10/1999 | Chenchik |
| 6,197,554 B1 | 3/2001 | Lin et al. |
| 7,479,472 B1 | 1/2009 | Harbury |
| 8,115,396 B2 | 2/2012 | Zhang |
| 8,673,562 B2 | 3/2014 | Drmanac |
| 8,771,951 B2 | 7/2014 | Hogan |
| 8,771,957 B2 | 7/2014 | Drmanac |
| 8,835,358 B2 | 9/2014 | Fodor et al. |
| 8,871,686 B2 | 10/2014 | Ghadessy et al. |
| 9,040,256 B2 | 5/2015 | Grunenwald et al. |
| 9,074,204 B2 | 7/2015 | Anderson et al. |
| 9,074,251 B2 | 7/2015 | Steemers et al. |
| 9,080,211 B2 | 7/2015 | Grunenwald et al. |
| 9,085,801 B2 | 7/2015 | Grunenwald et al. |
| 9,115,396 B2 | 8/2015 | Grunenwald et al. |
| 9,238,671 B2 | 1/2016 | Goryshin et al. |
| 9,290,808 B2 | 3/2016 | Fodor et al. |
| 9,315,857 B2 | 4/2016 | Fu et al. |
| 9,506,918 B2 | 11/2016 | Fischer et al. |
| 9,637,784 B2 | 5/2017 | Drmanac |
| 9,708,659 B2 | 7/2017 | Fodor et al. |
| 9,727,810 B2 | 8/2017 | Fodor et al. |
| 9,790,476 B2 | 10/2017 | Gloeckner et al. |
| 9,816,137 B2 | 11/2017 | Fodor et al. |
| 9,845,502 B2 | 12/2017 | Fodor et al. |
| 10,002,316 B2 | 6/2018 | Fodor et al. |
| 10,035,992 B2 | 7/2018 | Gloeckner et al. |
| 10,059,989 B2 | 8/2018 | Giresi et al. |
| 10,144,950 B2 | 12/2018 | Nolan |
| 10,150,963 B2 | 12/2018 | Hindson et al. |
| 10,150,964 B2 | 12/2018 | Hindson et al. |
| 10,150,995 B1 | 12/2018 | Giresi et al. |
| 10,155,981 B2 | 12/2018 | Brenner et al. |
| 10,184,122 B2 | 1/2019 | Grunenwald et al. |
| 10,240,197 B1 | 3/2019 | Brenner et al. |
| 10,280,459 B1 | 3/2019 | Brenner et al. |

(Continued)

FOREIGN PATENT DOCUMENTS

| | | |
|---|---|---|
| EP | 3234602 | 10/2017 |
| EP | 3234602 B1 | 8/2021 |

(Continued)

OTHER PUBLICATIONS

U.S. Appl. No. 62/094,917, filed Dec. 19, 2014; Nolan.

(Continued)

*Primary Examiner* — Kaijiang Zhang
(74) *Attorney, Agent, or Firm* — Christensen O'Connor Johnson Kindness PLLC

(57) ABSTRACT

Methods of uniquely labeling or barcoding molecules within a cell, a plurality of cells, and/or a tissue are provided. Kits for uniquely labeling or barcoding molecules within a cell, a plurality of cells, and/or a tissue are also provided. The molecules to be labeled may include, but are not limited to, RNAs, cDNAs, DNAs, proteins, peptides, and/or antigens.

23 Claims, 15 Drawing Sheets

Specification includes a Sequence Listing.

(56) References Cited

U.S. PATENT DOCUMENTS

| | | |
|---|---|---|
| 10,287,574 B2 | 5/2019 | Goryshin et al. |
| 10,337,062 B2 | 7/2019 | Giresi et al. |
| 10,385,323 B2 | 8/2019 | Gloeckner et al. |
| 10,544,403 B2 | 1/2020 | Gloeckner et al. |
| 10,557,133 B2 | 2/2020 | Steemers et al. |
| 10,557,166 B2 | 2/2020 | Drmanac et al. |
| 10,619,207 B2 | 4/2020 | Giresi et al. |
| 10,626,442 B2 | 4/2020 | Nolan |
| 10,697,013 B1 | 6/2020 | Brenner et al. |
| 10,738,357 B2 | 8/2020 | Giresi et al. |
| 10,752,894 B2 | 8/2020 | Lebofsky et al. |
| 10,760,121 B2 | 9/2020 | Hansen et al. |
| 10,774,367 B2 | 9/2020 | Fraser et al. |
| 10,844,372 B2 | 11/2020 | Belhocine et al. |
| 10,889,859 B2 | 1/2021 | Giresi et al. |
| 10,894,980 B2 | 1/2021 | Chen et al. |
| 10,900,065 B2 | 1/2021 | Seelig et al. |
| 10,982,256 B2 | 4/2021 | Nolan |
| 10,982,271 B2 | 4/2021 | Bava et al. |
| 10,995,362 B2 | 5/2021 | Dallett et al. |
| 11,008,567 B2 | 5/2021 | Goryshin et al. |
| 11,118,175 B2 | 9/2021 | Grunenwald et al. |
| 11,142,786 B2 | 10/2021 | Fraser et al. |
| 11,155,810 B2 | 10/2021 | Belhocine et al. |
| 11,168,355 B2 | 11/2021 | Seelig et al. |
| 11,180,804 B2 | 11/2021 | Chen et al. |
| 11,198,866 B2 | 12/2021 | Belhocine et al. |
| 11,214,794 B2 | 1/2022 | Nolan |
| 11,248,227 B2 | 2/2022 | Lebofsky et al. |
| 11,255,847 B2 | 2/2022 | Schnall-Levin |
| 11,427,856 B2 | 8/2022 | Seelig et al. |
| 11,512,341 B1 | 11/2022 | Nolan |
| 11,519,032 B1 | 12/2022 | Giresi et al. |
| 11,555,216 B2 | 1/2023 | Seelig et al. |
| 11,560,585 B2 | 1/2023 | Nolan |
| 11,566,278 B2 | 1/2023 | Nolan |
| 11,597,974 B2 | 3/2023 | Giresi et al. |
| 11,634,751 B2 | 4/2023 | Seelig et al. |
| 11,634,752 B2 | 4/2023 | Nolan |
| 11,639,519 B1 | 5/2023 | Seelig et al. |
| 11,667,956 B2 | 6/2023 | Nolan |
| 11,692,214 B2 | 7/2023 | Nolan |
| 11,708,599 B2 | 7/2023 | Nolan |
| 11,732,290 B2 | 8/2023 | Nolan |
| 11,781,171 B1 | 10/2023 | Nolan |
| 11,987,838 B2 | 5/2024 | Seelig et al. |
| 12,043,864 B2 | 7/2024 | Seelig |
| 2006/0034826 A1 | 2/2006 | Carreno |
| 2006/0099592 A1 | 5/2006 | Freskgard |
| 2006/0099626 A1 | 5/2006 | Harbury |
| 2006/0177833 A1 | 8/2006 | Brenner |
| 2009/0209430 A1 | 8/2009 | Rasmussen |
| 2009/0264300 A1 | 10/2009 | Franch |
| 2012/0220494 A1 | 8/2012 | Samuels et al. |
| 2013/0203605 A1 | 8/2013 | Shendure |
| 2013/0274117 A1 | 10/2013 | Church et al. |
| 2014/0099637 A1 | 4/2014 | Nolan et al. |
| 2014/0256597 A1 | 9/2014 | He |
| 2014/0309118 A1 | 10/2014 | Bang et al. |
| 2014/0309119 A1 | 10/2014 | Jacobsen et al. |
| 2015/0298091 A1 | 10/2015 | Weitz et al. |
| 2015/0299784 A1 | 10/2015 | Fan et al. |
| 2015/0329852 A1 | 11/2015 | Nolan |
| 2015/0376608 A1 | 12/2015 | Kaper et al. |
| 2016/0060691 A1 | 3/2016 | Giresi |
| 2016/0115471 A1 | 4/2016 | Kim |
| 2016/0122753 A1 | 5/2016 | Mikkelsen et al. |
| 2016/0138086 A1 | 5/2016 | Seelig et al. |
| 2016/0194699 A1 | 7/2016 | Borodina et al. |
| 2016/0251697 A1 | 9/2016 | Nolan |
| 2016/0289737 A1 | 10/2016 | Belyaev |
| 2016/0378916 A1 | 12/2016 | Drmanac et al. |
| 2017/0009274 A1 | 1/2017 | Abate et al. |
| 2017/0321251 A1 | 11/2017 | Nolan |
| 2017/0362642 A1 | 12/2017 | Nolan et al. |
| 2018/0135042 A1 | 5/2018 | Rokhsar |
| 2018/0320241 A1 | 11/2018 | Nolan |
| 2020/0157603 A1 | 5/2020 | O'Huallachain et al. |
| 2020/0208197 A1 | 7/2020 | Nolan |
| 2021/0002733 A1 | 1/2021 | Nolan |
| 2021/0040538 A1 | 2/2021 | Nolan |
| 2021/0189463 A1 | 6/2021 | Seelig |
| 2021/0310046 A1 | 10/2021 | Seelig |
| 2022/0049286 A1 | 2/2022 | Dallett et al. |
| 2022/0056503 A1 | 2/2022 | Seelig |
| 2022/0056515 A1 | 2/2022 | Bava et al. |
| 2022/0333158 A1 | 10/2022 | Seelig |
| 2023/0049314 A1 | 2/2023 | Nolan |
| 2023/0081326 A1 | 3/2023 | Nolan |
| 2023/0167484 A1 | 6/2023 | Nolan |
| 2023/0193351 A1 | 6/2023 | Georg |
| 2023/0227891 A1 | 7/2023 | Seelig |
| 2023/0265487 A1 | 8/2023 | Seelig |
| 2023/0392192 A1 | 12/2023 | Seelig |
| 2023/0392193 A1 | 12/2023 | Seelig |
| 2023/0399680 A1 | 12/2023 | Seelig |
| 2024/0002907 A1 | 1/2024 | Seelig |
| 2024/0102080 A1 | 3/2024 | Seelig |
| 2024/0110226 A1 | 4/2024 | Seelig |
| 2024/0110227 A1 | 4/2024 | Seelig |
| 2024/0301467 A1 | 9/2024 | Seelig |
| 2024/0336953 A1 | 10/2024 | Seelig et al. |

FOREIGN PATENT DOCUMENTS

| | | |
|---|---|---|
| WO | 2010094036 | 8/2010 |
| WO | 2012/106385 A2 | 8/2012 |
| WO | 2012129363 A2 | 9/2012 |
| WO | 2013036810 | 3/2013 |
| WO | 2014026032 A2 | 2/2014 |
| WO | 2014/137193 | 9/2014 |
| WO | 2014/144495 A1 | 9/2014 |
| WO | 2014142850 A1 | 9/2014 |
| WO | 2014/182528 | 11/2014 |
| WO | 2014/201273 A1 | 12/2014 |
| WO | 2016/100976 A2 | 6/2016 |
| WO | 2017044893 A1 | 3/2017 |
| WO | 2019/236599 A2 | 12/2019 |

OTHER PUBLICATIONS

U.S. Appl. No. 62/094,919, filed Dec. 19, 2014; Nolan.

U.S. Appl. No. 62/094,924, filed Dec. 19, 2014; Nolan.

Yozwiak et al., 2010, "Human Enterovirus 109: a Novel Interspecies Recombinant Enterovirus Isolated from a Case of Acute Pediatric Respiratory Illness in Nicaragua," 84(18) J. Virology 9047 (Sep. 2010).

Zhang et al., 2012, "Strand-specific libraries for high throughput RNA sequencing (RNA-Seq) prepared without poly(A) selection," 3(9) Silence (2012).

Zhong et al., 2011, "High-Throughput Illumina Strand-Specific RNA Sequencing Library Preparation," Cold Spring Harbor Protocols 940 (Aug. 2011).

Islam et al., 2011, "Characterization of the single-cell transcriptional landscape by highly multiplex RNA-seq," 21(7) Genome Research 1160 (May 4, 2011).

Civil Action No. 1:22-CV-01597-CJB; Scale Biosciences, Inc.'S Initial Invalidity Contentions; 501 pages.

Civil Action No. 22-1597-CJB; Parse Biosciences Inc.'S First Supplemental and Amended Invalidity Contentions; Sep. 15, 2023; 33 pages.

Eberwine, J. et al., "Analysis of gene expression in single live neurons," Proc. Natl. Acad. Sci. USA, vol. 89. pp. 3010-3014. Apr. 1992, Neurobiology.

Hrvatin, S. et al., "Maris: Method for Analyzing RNA following Intracellular Sorting," PLoS ONE 9(3): e89459. doi:10.1371/journal.pone.0089459.

O'dell, et al., "Amplification of mRNAs from Single, Fixed, Tunel-Positive Cells," Oct. 1998, BioTechniques 25: 566-570 (1998).

Sasagawa, Y. et al., "Quartz-Seq: a highly reproducible and sensitive single-cell RNA sequencing method, reveals nongenetic gene-

(56) References Cited

OTHER PUBLICATIONS expression heterogeneity," Genome Biology 2013, 14:R31. <http://genomebiology.com/2013/14/4/R31>.

Schlosser, K. and Y. Li, "Tracing Sequence Diversity Change of RNA-Cleaving Deoxyribozymes under Increasing Selection Pressure during in Vitro Selection," Biochemistry 2004, 43, 9695-9707.

Lee, M-C. W. et al., "Single-cell analyses of transcriptional heterogeneity during drug tolerance transition in cancer cells by RNA sequencing," PNAS; published online Oct. 22, 2014; E4726-E4735.

Non-Final Office Action mailed on Aug. 22, 2024 in U.S. Appl. No. 18/455,133, filed Aug. 24, 2023; pp. 1-17.

Non-Final Office Action mailed on Aug. 14, 2024 in U.S. Appl. No. 18/536,721, filed Dec. 12, 2023; pp. 1-24.

Brenner et al., "In vitro cloning of complex mixtures of DNA on microbeads: Physical separation of differentially expressed cDNAs," 97(4):1665-70 PNAS (Feb. 2000).

Burzio et al., "Expression of a family of noncoding mitochondrial RNAs distinguishes normal from cancer cells," 106(23):9430-34 Proc. Natl. Acad. Sci. U.S.A. (Jun. 9, 2009).

Hoffman et al., "DNA bar coding and pyrosequencing to identify rare HIV drug resistance mutations," 35(13):e91 Nucleic Acids Research (Jun. 18, 2007).

TruSeq® DNA Sample Preparation Guide, Jul. 2012.

Kurimoto, K. and M. Saitou, "Single-cell cDNA microarray profiling of complex biological processes of differentiation," 20 Current Opinion in Genetics & Development 470 (Jul. 7, 2010).

Kurimoto, K. et al., "An improved single-cell cDNA amplification method for efficient high-density oligonucleotide microarray analysis," 34(5) Nucleic Acids Research e42 (received Jan. 17, 2006; published Mar. 17, 2006).

Liu, R. et al., Combinatorial peptide library methods for immunobiology research, 31:11-30 Experimental Hematology (Jan. 2003).

Marks, H. et al., "Insightful Tales from Single Embryonic Cells," 6 Cell Stem Cell 397 (May 7, 2010).

Rice, S. C. et al., "Genotoxicity of Therapeutic Intervention in Children with Acute Lymphocytic Leukemia," 64(13):4464-71 Cancer Research (Jul. 1, 2004).

Scott, J. K. and G. P. Smith, "Searching for Peptide Ligands with an Epitope Library," 249:386-90 (Jul. 27, 1990).

Shrivastav, N. et al. "Chemical biology of mutagenesis and DNA repair: cellular responses to DNA alkylation," 31(1):59-70 Carcinogenesis (Oct. 29, 2009).

Staerk, J. et al., "Reprogramming of peripheral blood cells to induced pluripotent stem cells," 7(1):20-24 Cell Stem Cell (Jul. 2, 2010).

Storch, G. A. "Special Section: Medical Microbiology," 31(3):739-51 Clin. Infect. Dis. (Sep. 2000).

Tang, S. and T. Huang, "Characterization of mitochondrial DNA heteroplasmy using a parallel sequencing system," 48(4):287-96 Biotechniques (Apr. 2010).

Tang, F. et al., "Tracing the Derivation of Embryonic Stem Cells from the Inner Cell Mass by Single-Cell RNA-Seq Analysis," 6 Cell Stem Cell 468 (May 7, 2010).

Tang, F. et al., "Development and applications of single cell transcriptome analysis," 8(4S) Nature Methods Supplement 56 (Apr. 2011).

Tietjen, I. et al., "Single-Cell Transcriptional Analysis of Neuronal Progenitors," 38 Neuron 161 (Apr. 24, 2003.

Urnov, F. D. et al., "Genome editing with engineered zinc finger nucleases," 11(9):636-46 Nature Reviews Genetics (Sep. 2010).

Villegas, J. et al., "Expression of a novel non-coding mitochondrial RNA in human proliferating cells," 35(21):7336-47 Nucleic Acids Res. (Oct. 25, 2007).

Watzinger, F. et al., "Real-Time Quantitative PCR Assays for Detection and Monitoring of Pathogenic Human Viruses in Immunosuppressed Pediatric Patients," 42(11):5189-98 J. Clin. Microbiology (Nov. 2004).

Moignard, V. et al., "Decoding the regulatory network of early blood development from single-cell gene expression measurements," Nature Biotechnology, 33(3):269-276, Mar. 2015.

Moriyama, M. et al., "Complement Receptor 2 Is Expressed in Neural Progenitor Cells and Regulates Adult Hippocampal Neurogenesis," The Journal of Neuroscience, 31(11):3981-3989, Mar. 16, 2011.

Murthy, M. et al., "Transcription factor Runx1 inhibits proliferation and promotes developmental maturation in a selected population of inner olfactory nerve layer olfactory ensheathing cells," Gene, 540:191-200, 2014.

Nagalski, A. et al., "Molecular anatomy of the thalamic complex and the underlying transcription factors," Brain Struct. Funct., 221:2493-2510, 2016.

Nakashima, K. et al., "Cerebellar Granule Cells are Predominantly Generated by Terminal Symmetric Divisions of Granule Cell Precursors," Developmental Dynamics, 244:748-758, 2015.

Nielsen, J.V. et al., "Zbtb20-Induced CA1 Pyramidal Neuron Development and Area Enlargement in the Cerebral Midline Cortex of Mice," Cerebral Cortex, 20:1904-1914, Aug. 2010.

Ogawa, M. et al., "The reeler Gene-Associated Antigen on Cajal-Retzius Neurons Is a Crucial Molecule for Laminar Organization of Cortical Neurons," Neuron, 14:899-912, May 1995.

Pedregosa, F. et al., "Scikit-learn: Machine Learning in Python," Journal of Machine Learning Research, 12:2825-2830, published Oct. 2011.

Petracca, Y.L. et al., "The late and dual origin of cerebrospinal fluid-contacting neurons in the mouse spinal cord," Development, 143:880-891, 2016.

Picelli, S. et al., "Smart-seq2 for sensitive full-length transcriptome profiling in single cells," Nature Methods, 10:1096-1098, 2013.

Rosenberg, A.B. et al., "Scaling single cell transcriptomics through split pool barcoding," BioRxiv, 2017, available at: https://doi.org/10.1101/105163.

Rosenberg, A.B. et al., "Single-cell profiling of the developing mouse brain and spinal cord with split-pool barcoding," Science, 360(6385):176-182, 2018.

Rosenberg, A.B. et al., "Single-cell profiling of the developing mouse brain and spinal cord with split-pool barcoding—supplementary materials," retrieved from the Internet at https://science.sciencemag.org/content/sci/suppl/2018/03/14/science.aam8999.DC1/aam8999_Rosenberg_SM.pdf, Apr. 13, 2018, 55 pages.

Saab, A.S. et al., "Bergmann Glial AMPA Receptors are Required for Fine Motor Coordination," Science, 337:749-753, Aug. 10, 2012.

Salero, E. and Hatten, M.E., "Differentiiation of ES cells into cerebellar neurons," Proc. Natl. Acad. Sci. USA, 104(8):2997-3002, Feb. 20, 2007.

Sánchez-Mendoza, E. et al., "Review: Could neurotransmitters influence neurogenesis and neurorepair after stroke?" Neuropathology and Applied Neurobiology, 39:722-735, 2013.

Sang, L. et al., "Control of the Reversibility of Cellular Quiescence by the Transcriptional Repressor HES1," Science, 321:1095-1100, Aug. 22, 2008.

Schilling, K. et al., "Besides purkinje cells and granule neurons: an appraisal of the cell biology of the interneurons of the cerebellar cortex," Histochem. Cell Biol., 130:601-615, 2008.

Seal, R.P. et al., "Injury-induced mechanical hypersensitivity requires C-low threshold mechanoreceptors," Nature, 462:651-655, Dec. 3, 2009.

Shekhar, K. et al. "Comprehensive Classification of Retinal Bipolar Neurons by Single-Cell Transcriptomics," Cell, 166:1308-1323, Aug. 25, 2016.

Song, H. et al., "Ascl1 and Helt act combinatorially to specific thalamic neuronal identity by repressing Dlxs activation," Developmental Biology, 398:280-291, 2015.

Sudarov, A. and Joyner, A.L., "Cerebellum morphogenesis: the foliation pattern is orchestrated by multi-cellular anchoring centers," Neural Development, 2:26, 21 pages, Dec. 3, 2007.

Tasic, B. et al., "Adult mouse cortical cell taxonomy revealed by single cell transcriptomics," Nature Neuroscience, 19(2):335-346, Feb. 2016.

Thompson, C.L. et al., "A High-Resolution Spatiotemporal Atlas of Gene Expression of the Developing Mouse Brain," Neuron, 83:309-323, Jul. 16, 2014.

(56) References Cited

OTHER PUBLICATIONS

Thomsen, E.R. et al., "Fixed single-cell transcriptomic characterization of human radial glial diversity," Nature Methods, 13(1):87-93, Jan. 2016.
Tirosh, I. et al., "Dissecting the multicellular ecosystem of metastatic melanoma by single-cell RNA-seq," Science, 352(6282):189-196, Apr. 8, 2016, corrected Feb. 1, 2019.
Tritsch, N.S. et al., "Dopaminergic neurons inhibit striatal output through non-canonical release of GABA," Nature, 490:262-266, Oct. 11, 2012.
Qiu, X. et al., "Reversed graph embedding resolves complex single-cell trajectories," Nature Methods, 14(10):979-982, Oct. 2017.
Valcanis, H. and Tan, S-S., "Layer Specification of Transplanted Interneurons in Developing Mouse Neocortex," The Journal of Neuroscience, 23(12):5113-5122, Jun. 15, 2003.
Van Der Maaten, L., "Accelerating t-SNE using Tree-Based Algorithms," Journal of Machine Learning Research, 15:3221-3245, published Oct. 2014.
Venteicher, A.S. et al., "Decoupling genetics, linearges, and microenvironment in IDH-mutant gliomas by single-cell RNA-seq," Science, 335:eaai8478, 1391, Mar. 31, 2017.
Weisheit, G. et al., "Postnatal development of the murine cerebellar cortex: formation and early dispersal of basket, stellate and Golgi neurons," European Journal of Neuroscience, 24:466-478, 2006.
Wisniewska, M.B. et al., "LEF1/beta-Catenin Complex Regulates Transcription of the Cav3.1 Calcium Channel Gene (Cacna1g) in Thalamic Neurons of the Adult Brain," The Journal of Neuroscience, 30(14):4957-4969, Apr. 7, 2010.
Xie, Z. et al., "Zbtb20 is essential for the specification of CA1 field identity in the developing hippocampus," Proc. Natl. Acad. Sci. USA, 107(14):6510-6515, Apr. 6, 2010.
Yang, M.J. e tal., "Mitral and Tufted Cells Are Potential Cellular Targets of Nitration in the Olfactory Bulb of Aged Mice," PLoS One, 8(3):e59673, 11 pages, Mar. 2013.
Yao, Z. et al., "A Single-Cell Roadmap of Lineage Bifurcation in Human ESC Models of Embryonic Brain Development," Cell Stem Cell, 20:120-134, Jan. 15, 2017.
Zeisel, A. et al., "Cell types in the mouse cortex and hippocampus revealed by single-cell RNA-seq," Science, 347(6226):1138-1142, Mar. 6, 2015.
Zhao, C. et al., "Mechanisms and Functional Implications of Adult Neurogenesis," Cell, 132:645-660, Feb. 22, 2008.
Zheng, C. et al., "Landscape of Infiltrating T Cells in Liver Cancer Revealed by Single-Cell Sequencing," Cell, 169:1342-1356, Jun. 15, 2017.
Zheng, G.X.Y. et al., "Massively parallel digital transcriptional profiling of single cells," Nature Communications, 8:14049 (12 pages), published Jan. 16, 2017.
Zorita, E. et al., "Starcode: sequence clustering based on all-pairs search," Bioinformatics, 31(12):1913-1919, 2015.
Shah, S. et al., "In Situ Transcription Profiling of Single Cells Reveals Spatial Organization of Cells in the Mouse Hippocampus," Neuron, 92:342-357, Oct. 19, 2016.
Shimizu et al., 2014, "Qualitative De Novo Analysis of Full Length cDNA and Quantitative Analysis of Gene Expression for Common Marmoset (*Callithrix jacchus*) Transcriptomes Using Parallel Long-Read Technology and Short-Read Sequencing," 9(6) PLoS One e100936 (Jun. 2014).
Swaroop & Xu, 1993, cDNA libraries from human tissues and cell lines, 64 Cytogenetic Cell Genetics 292 (1993).
Tang et al., 2009, "mRNA-Seq whole-transcriptome analysis of a single cell," 6(5) Nature Methods 377 (Apr. 6, 2009).
Treutlein et al., 2014, Reconstruction lineage hierarchies of the distal lung epithelium using single-cell RNA-seq, 509 Nature 371 (May 15, 2014).
Vivancos, et al., 2010, "Strand-specific deep sequencing of the transcriptome," 20 Genome Research 989 (Jun. 2, 2010).
Vo & Jedlicka, 2014, "Protocols for metagenomic DNA extraction and Illumina amplicon library preparation for fecal and swab samples," Molecular Ecology Resources (Apr. 2014).
Wuest et al., 2013, "Cell-specific expression profiling of rare cell types as exemplified by its impact on our understanding of female gametophyte development," 16(1) Current Opinion in Plant Biology 41 (2013).
Ying et al., 1999, "Generation of Full-Length cDNA Library from Single Human Prostate Cancer Cells," 27(3) Biotechniques 410-14 (published Sep. 1999).
Abraham, H. et al., "p73 and Reelin in Cajal-Retzius Cells of the Developing Human Hippocampal Formation," Cerebral Cortex, 14(5):484-495, May 2004.
Alcamo, E.A. et al., "Satb2 Regulates Callosal Projection Neuron Identity in the Developing Cerebral Cortex," Neuron, 57:364-377, Feb. 7, 2008.
Alifragis, P. et al., "Lhx6 Regulates the Migration of Cortical Interneurons from the Ventral Telencephalon But Does Not Specify their GABA Phenotype," The Journal of Neuroscience, 24(24):5643-5648, Jun. 16, 2004.
Altman, J. and Bayer, S.A., "Development of the Precerebellar Nuclei in the Rat: I. The Precerebellar Neuroepithelium of the Rhombencephalon," The Journal of Comparative Neurology, 257:477-489, 1987.
Afsari, Z.H. et al., "Alteration of Glial Fibrillary Acidic Proteins Immunoreactivity in Astrocytes of the Spinal Cord Diabetic Rats," Anat. Rec. Adv. Integr. Anat. Evol. Biol., 291:390-399, 2008.
Belgard, T.G. et al., "A Transcriptomic Atlas of Mouse Neocortical Layers," Neuron, 71:605-616, Aug. 25, 2011.
Bonnet, F. et al., "Structure and Cellular Distribution of Mouse Brain Testican," The Journal of Biological Chemistry, 271(8):4373-4380, Feb. 23, 1996.
Brumovsky, P.R., "VGLUTs in Peripheral Neurons and the Spinal Cord: Time for a Review," ISRN Neurology, 213:829753, 28 pages, 2013.
Butovsky, O. et al., "Identification of a unique TGF-$\beta$-dependent molecular and functional signature in microglia," Nature Neuroscience, 17(1):131-143, Jan. 2014.
Cahoy, J.D. et al., "A Transcriptome Database for Astrocytes, Neurons, and Oligodendrocytes: A New Resource for Understanding Brain Development and Function," The Journal of Neuroscience, 28(1):264-278, Jan. 2, 2008.
Cao, J. et al., "Comprehensive single-cell transcriptional profiling of a multicellular organism," Science, 357(6352):661-667, Aug. 18, 2017.
Cembrowski, M.S. et al., "Hipposeq: a comprehensive RNA-seq database of gene expression in hippocampal principal neurons," eLife, 5:e14997, 22 pages, Apr. 26, 2016.
Chang, J.C. et al., "Mitotic Events in Cerebellar Granule Progenitor Cells That Expand Cerebellar Surface Area are Critical for Normal Cerebellar Cortical Lamination in Mice," J. Neuropathol. Exp. Neurol., 74(3):261-272, Mar. 2015.
Cheung, K-K. et al., "Dynamic expression of Dab2 in the mouse embryonic central nervous sytem," BMC Developmental Biology, 8:76, 11 pages, Aug. 4, 2008.
Chiu, Y-C. et al., "Foxp2 Regulates Neuronal Differentiation and Neuronal Subtype Specification," Developmental Neurobiology, 74:723-738, 2014.
Chuikov, S. et al., "Prdm16 promotes stem cell maintenance in multiple tissues, partly by regulating oxidative stress," Nature Cell Biology, 12(10):999-1006, Oct. 2010.
Corrales, J.D. et al., "The level of sonic hedgehog signaling regulates the complexity of cerebellar foliation," Development, 133(9):1811-1821, 2006.
Darmanis, S. et al., "A survey of human brain transcriptome diversity at the single cell level," Proc. Natl. Acad. Sci. USA, 112(23):7285-7290, Jun. 9, 2015.
Deangelis, M.M. et al., "Solid-phase reversible immobilization for the isolation of PCR Products," Nucleic Acids Research, 23(22):4742-4743, 1995.
Dobin, A. et al., "STAR: ultrafast universal RNA-seq aligner," Bioinformatics, 29(1):15-21, 2013.
Doyle, J.P. et al., "Application of a Translational Profiling Approach for the Comparative Analysis of CNS Cell Types," Cell, 135:749-762, Nov. 14, 2008.

(56) References Cited

OTHER PUBLICATIONS

D'Souza, C.A. et al., "Identification of a set of genes showing regionally enriched expression in the mouse brain," BMC Neuroscience, 9:66, 14 pages, Jul. 14, 2008.
Ehmsen, J.T. et al., "The astrocytic transporter SLC7A10 (Asc-1) mediates glycinergic inhibition of spinal cord motor neurons," Scientific Reports, 6:35592, 13 pages, Oct. 19, 2016.
Enjin, A. et al., "Identification of Novel Spinal Cholinergic Genetic Subtypes Disclose Chodl and Pitx2 as Markers for Fast Motor Neurons and Partition Cells," The Journal of Comparative Neurology, 518:2284-2304, 2010.
Erlander, M.G. and Tobin, A.J., "The Structural and Functional heterogeneity of Glutamic Acid Decarboxylase: A Review," Neurochemical Research, 16(3):215-226, 1991.
Ester, M. et al., "A Density-Based Algorithm for Discovering Clusters—A Density-Based Algorithm for Discovering Clusters in Large Spatial Databases with Noise," Proc. Second Int. Conf. Knowl. Discov. Data Min., pp. 226-231, 1996.
Extended European Search Report dated May 20, 2021, in corresponding European Patent Application No. 18858002.1, 7 pages.
Grün, D. et al., "Single-cell messenger RNA sequencing reveals rare intestinal cell types," Nature, 525:251-255, Sep. 10, 2015.
Habib, N. et al., "Div-Seq: Single-nucleus RNA-Seq reveals dynamics of rare adult newborn neurons," Science, 353(6302):925-928, Aug. 26, 2016.
Hashimshony, T. et al., "CEL-Seq: Single-Cell RNA-Seq by Multiplexed Linear Amplification," Cell Reports, 2:666-673, Sep. 27, 2012.
He, L. et al., "Analysis of the brain mural cell transcriptome," Scientific Repeorts, 6:35108, 13 pages, 2016.
Herculano-Houzel, S., "The human brain in numbers: a linearly scaled-up primate brain," Frontiers in Human Neuroscience, 3:31, 11 pages, Nov. 9, 2009.
Hesse, K. et al., "AP-2δ Is a Crucial Transcriptional Regulator of the Posterior Midbrain," PLoS One, 6(8):e23483, 12 pages, Aug. 2011.
Hickman, S.E. et al., "The microglial sensome revealed by direct RNA sequencing," Nature Neuroscience, 16(12):1896-1905, Dec. 2013.
Honoré, A. et al., "Isolation, Characterization, and Genetic Profiling of Subpopulations of Olfactory Ensheathing Cells from the Olfactory Bulb," Glia, 60:404-413, 2012.
International Search Report and Written Opinion mailed Mar. 27, 2019, for PCT International Patent Application No. PCT/US2018/052283, filed Sep. 21, 2018, 17 pages.
Iwano, T. et al., "Prox1 postmitotically defines dentate gyrus cells by specifying granule cell identity over CA3 pyramidal cell fate in the hippocampus," Development, 139(16):3051-3062, 2012.
Kawasawa, Y.I. et al., "RNA-seq analysis of developing olfactory bulb projection neurons," Molecular and Cellular Neuroscience, 74:78-86, 2016.
Knight, H.M. et al., "GRIK4/KA1 Protein Expression in Human Brain and Correlation with Bipolar Disorder Risk Variant Status," American Journal of Medical Genetics Part B, Neuropsychiatric Genetics, 159B:21-29, 2012.
Lacar, B. et al., "Nuclear RNA-seq of single neurons reveals molecular signatures of activation," Nature Communications, 7:11022, 13 pages, 2016.
Lake, B.B. et al., "Neuronal subtypes and diversity revealed by single-nucleus RNA sequencing of the human brain," Science, 352(6293):1586-1590, Jun. 24, 2016.
Lalancette-Hebert, M. et al., "Gamma motor neurons survive and exacerbate alpha motor neuron degeneration in ALS," Proc. Natl. Acad. Sci. USA, 113:E8316-E8325, published online Dec. 7, 2016.
Lavado, A. et al., "Prox1 Is Required for Granule Cell Maturation and Intermediate Progenitor Maintenance During Brain Neurogenesis," PLoS Biology, 8(8):e1000460, Aug. 2010.
Lein, E.S. et al., "Genome-wide atlas of gene expression in the adult mouse brain," Nature, 445:168-176, Jan. 11, 2007.
Levison, S.W. and Goldman, J.E., "Both Oligodendrocytes and Astrocytes Develop from Progenitors in the Subventricular Zone of Postnatal Rat Forebrain," Neuron, 10:201-212, Feb. 1993.
Lubeck, E. and Cai, L., "Single-cell systems biology by super-resolution imaging and combinatorial labeling," Nature Methods, 9(7):743-748, Jul. 2012.
Maricich, S.M. and Herrup, K., "Pax-2 Expression Defines a Subset of GABAergic Interneurons and Their Precursors in the Developing Murine Cerebellum," J. Neurobiol., 41:281-294, 1999.
Marques, S. et al., "Oligodendrocyte heterogeneity in the mouse juvenile and adult central nervous system," Science, 352(6291):1326-1329, Jun. 10, 2016.
Matcovitch-Natan, O. et al., "Mmicroglia development follows a stepwise program to regulate brain homeostasis," Science, 353(6301):aad8670-1-aad8670-12, 789, Aug. 19, 2016.
Miyashita, T. et al., "Neurotrophin-3 Is Involved in the Formation of Apical Dendritic Bundles in Cortical Layer 2 of the Rat," Cerebral Cortex, 20:229-240, Jan. 2010.
Adey, et al., In vitro, long-range sequence information for de novo genome assembly via transposase contiguity, Genome Res. 24, 2041-2049, 2014.
Adey, et al., Rapid, low-input, low-bias construction of shotgun fragment libraries by high-density in vitro transposition, Genome Biol. 11, R119, 2010.
Amini, et al., Haplotype-resolved whole-genome sequencing by contiguity-preserving transposition and combinatorial indexing, Nat. Genet. 46, 1343-1349, Dec. 2014.
Boyle, et al., High-Resolution Mapping and Characterization of Open Chromatin Across the Genome, Cell 132, 3110-322, Jan. 25, 2008.
Buenrostro, et al., Transposition of native chromatin for fast and sensitive epigenomic profiling of open chromatin, DNA-binding proteins and nucleosome position, Nat. Methods 10, 1213-1218, Dec. 2013.
Casanovich, et al., Multiplex singe-cell profiling of chromatin accessibilty by combinatorial cellular indexing, Science, vol. 348, Issue 6237, pp. 910-914, May 22, 2015.
Deng, et al., Single-Cell RNA-Seq Reveals Dynamic, Random Monoallelic Gene Expression in Mammalian Cells, Science, 343, 193-196, Jan. 10, 2014.
Fan, et al., Combinatorial labeling of single cells for gene expression cytometry, Science, vol. 347, Issue 6222, 1258367, Feb. 6, 2015.
Fu, et al., Counting individual DNA Molecules by the stochastic attachment of diverse labels, Proc Natl Acad Sci. May 31, 2011; 108(22): 9026-31.
Fu, et al., Molecular Indexing Enables quantitative targeted RNA sequencing and reaveals poor efficiencies in standard library preparations, Proc Natl Acad Sci. Feb. 4, 2014; 111(5); 1891-1896.
Gole, et al., Massively Parallel Polymerase Cloning and Genome Sequencing of Single Cells Using Nanoliter Microwells, Nat. Biotechnol. 31, 1126-1132, Dec. 2013.
Jaitin, et al., Massively Parallel Single-Cell RNA-Seq for Marker-Free Decomposition of Tissues into Cell Types, Science 343, 776-779, Feb. 14, 2014.
Kivioja, et al., Counting absolute numbers of molecules using unique molecular identifiers, Nature Methods, Jan. 2012, vol. 9, No. 1, 72-74.
Klein, et al., Droplet Barcoding for Single-Cell Transcriptomics Applied to Embryonic Stem Cells, May 21, 2015, Cell 161, 1187-1201.
Macosko, et al., Highly Parallel Genome-Wide Expression Profiling of Individual Cells Using Nanoliter Droplets, Cell, 161, 1202-1214, May 21, 2015.
Mortazavi, et al., Mapping and quantifying mammalian transcriptomes by RNA-Seq, Nat Methods 5(7): 621-628, May 30, 2008.
Nagano, et al., Single-Cell Hi-C Reveals Cell-to-Cell Variability in Chromosome Structure, Nature 502, 59-64, Oct. 3, 2013.
Navin, et al., Tumour evolution inferred by single-cell sequencing, Nature 472, 90-94, Apr. 7, 2011.
Pan, et al., Single Cell Analysis: from Technology to Biology and Medicine, Single Cell Biol. 3, 106, 2014.

(56) References Cited

OTHER PUBLICATIONS

Regev, et al., The Human Cell Atlas, www.genome.gov/Multimedia/slides/GSPFuture2014/10_Regev.pdf.

Rotem, et al., High-Throughput Single-Cell Labeling (Hi-SCL) for RNA-Seq Using Drop-Based Microfluidics, PLoS ONE 10(5): e0116328, May 22, 2015.

Saliba, et al., Single-cell RNA-seq: advances and future challenges, Nucleic Acids Res. 42, 8845-8860, Jul. 22, 2014.

Shalek, et al., Single-Cell transcriptomics reveals bimiodality in expression and splicing in immune cells, Nature 498, 236-240, Jun. 13, 2013.

Shiroguchi, et al., Digital RNA sequencing minimizes sequence-dependent bias and amplification noise with optimized single-molecule barcodes, Proc Natl Acad Sci. Jan. 24, 2012; 109(4): 1347-52.

Smallwood, et al., Single-Cell Genome-Wide Bisulfite Sequencing for Assessing Epigenetic Heterogeneity, Nat. Methods 11, 817-820, Aug. 2014.

Stergachis, et al., Developmental Fate and Cellular Maturity Encoded in Human Regulatory DNA Landscapes, Cell 154, 888-903 Aug. 15, 2013.

The Encode Project Consortium, et al., An Integrated encyclopedia of DNA elements in the human genome, Nature 489, 57-74, 2012.

Thurman, et al., The Accessible Chromatin Landscape of the Human Genome, Nature 489, 75-82, Sep. 6, 2012.

Trapnell, et al., The Dynamics and Regulators of Cell Fate Decisions are Revealed by Pseudotemporal Ordering of Single Cells, Nat. Biotechnol. 32, 381-386, Apr. 2014.

Wu, et al., Quantitative Assessment of Single-Cell RNA-sequencing methods, Nat. Methods 11, 41-46, Jan. 2014.

Yang, et al., Global survey of escape from X inactivation by RNA-sequencing in mouse, Genome Res. 20, 614-622, 2010.

Jaitin, et al., "Massively Parallel Single-Cell RNA-Seq for Marker-Free Decomposition of Tissues into Cell Types," Science, 343(6172):776-779 online Supplement, 2014.

Matsuda, et al., "Comparison of Fixation Methods for Preservation of Morphology, RNAs, and Proteins From Paraffin-Embedded Human Cancer Cell-Implanted Mouse Models," Journal of Histochemistry & Cytochemistry, 59(1):68-75, 2011.

Burton, et al., 2013, "Chromosome-scale scaffolding of de novo genome assemblies based on chromatin interactions," 31(12) Nature Biotechnology 1119 (Nov. 3, 2013).

Cao, et al., 2017, "Comprehensive single cell transcriptional profiling of a multicellular organism by combinatorial indexing," bioRxiv, Cold Spring Harbor Laboratory; Feb. 2, 2017; doi: https://doi.org/10.1101/104844.

Croucher, et al., 2009, "A simple method for directional transcriptome sequencing using Illumina technology," 37(22) Nucleic Acids Research e148 (Oct. 8, 2009).

Eberwine, et al., 2014, "The promise of single-cell sequencing," 11(1) Nat. Methods 25 (Jan. 2014).

Gertz, et al., 2011, "Transposase mediated construction of RNA-seq libraries," 22 Genome Research 134-141 (published Nov. 29, 2011).

Gomez-Lozano, et al., 2012, "Genome-wide identification of novel small RNAs in Pseudomonas aeruginosa," 14(8) Env't Microbiology 2006 (Apr. 2012).

Gupta and Gupta, 2014, "Next Generation Sequencing and Its Applications," Animal Biotechnology. Models in Discovery and Translation (Ashish S. Verma and Anchal Singh, eds., Academic Press, Oxford) (2014).

Islam et al., 2013, "Quantitative single-cell RNA-seq with unique molecular identifiers," Nature Methods (Dec. 22, 2013).

Lee et al., 2014, "Highly Multiplexed Subcellular RNA Sequencing in Situ," 343 Science 1360-1363 (published Feb. 27, 2014).

Ligasová and Koberna, 2010, "In situ reverse transcription: the magic of strength and anonymity," 38(16) Nucleic Acids Research e167 (published Jul. 13, 2010).

Mamanova et al., 2010, "FRT-seq: Amplification-free, strand-specific, transcriptome sequencing," 7(2) Nature Methods 130 (Feb. 2010).

McDavid et al., 2012, "Data exploration, quality control and testing in single-cell qPCR," 29(4) Bioinformatics 461 (Dec. 24, 2012).

Miller et al., 2009, "TU-tagging: cell type specific RNA isolation from intact complex tissues," 6(6) Nature Methods 439 (Jun. 2009).

Picelli et al., 2014, "Full-length RNA-seq from single cells using Smart-seq2," Nature Protocols 171 (Jan. 2, 2014).

Plessy et al., 2012, "Population transcriptomics with single-cell resolution: A new field made possible by microfluidics," 35(2) Bioessays 131 (2012).

Politz & Singer, 1999, "In situ reverse transcription for detection of hybridization between oligonucleotides and their intracellular targets," Methods Jul. 1999;18(3):281-5.

Schmid et al., 2012, "A Powerful Method for Transcriptional Profiling of Specific Cell Types in Eukaryotes: Laser-Assisted Microdissection and RNA Sequencing," 7(1) PLoS ONE e29685 (Jan. 26, 2012).

Office Action (Notice of Allowance and Fees Due (PTOL-85)) dated Sep. 27, 2024 for U.S. Appl. No. 17/814,771 (pp. 1-4).

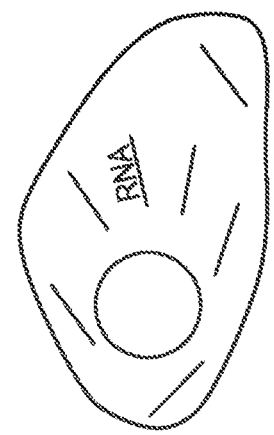
FIG. 2A
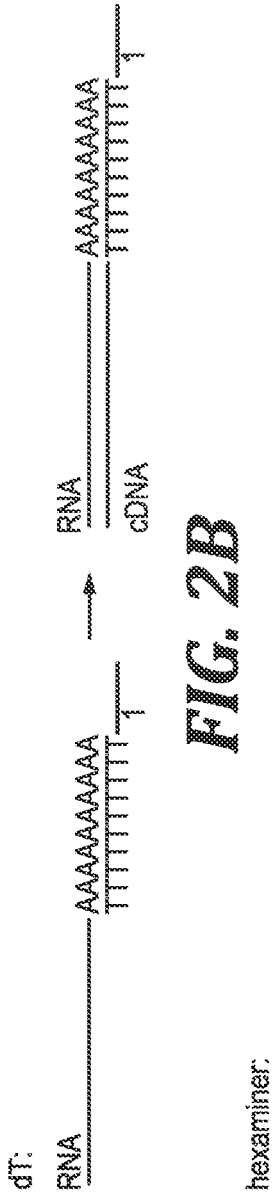
FIG. 2B
FIG. 2C
FIG. 2D
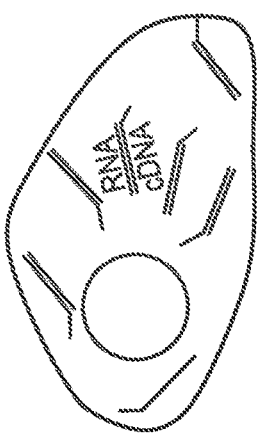
FIG. 2E

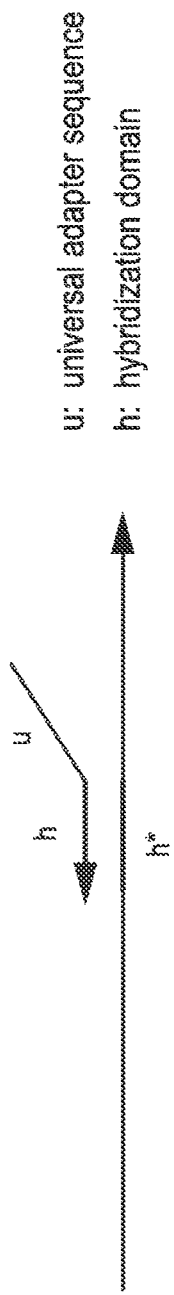
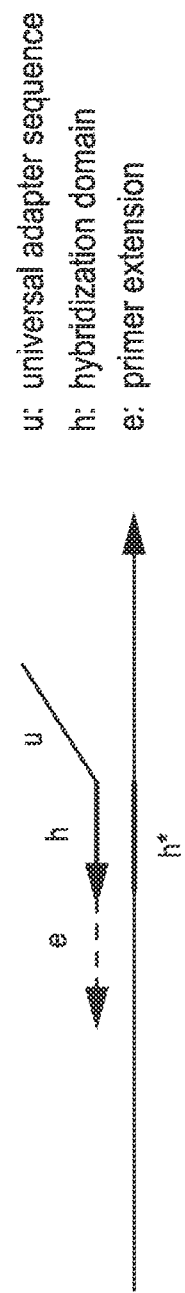

NBAAAAAAAAAAAAAAAACGAATGCTCTGGCCT (SEQ ID NO:1)

NVTTTTTTTTTTTTTTTGCTTACGAGACCGGA (SEQ ID NO:2)

BC_0055_dT(15)VN-S0 dT(15)NV | s0

10  20  30

```
                            SEQUENCE LISTING

Sequence total quantity: 15
SEQ ID NO: 1            moltype = DNA  length = 32
FEATURE                 Location/Qualifiers
source                  1..32
                        mol_type = other DNA
                        organism = synthetic construct
                        note = Reverse transcription primer, top strand
misc_difference         1
                        note = misc_feature - n is a, c, g, or t
SEQUENCE: 1
nbaaaaaaaa aaaaaaacga atgctctggc ct                                     32

SEQ ID NO: 2            moltype = DNA  length = 32
FEATURE                 Location/Qualifiers
source                  1..32
                        mol_type = other DNA
                        organism = synthetic construct
                        note = Reverse transcription primer, bottom strand
misc_difference         32
                        note = misc_feature - n is a, c, g, or t
SEQUENCE: 2
aggccagagc attcgttttt tttttttttt vn                                     32

SEQ ID NO: 3            moltype = DNA  length = 30
FEATURE                 Location/Qualifiers
source                  1..30
                        mol_type = other DNA
                        organism = synthetic construct
                        note = BC_0056_S0-S1
SEQUENCE: 3
cgaatgctct ggccttcgga cgatcatggg                                        30

SEQ ID NO: 4            moltype = DNA  length = 38
FEATURE                 Location/Qualifiers
source                  1..38
                        mol_type = other DNA
                        organism = synthetic construct
                        note = Round 1 barcodes
misc_difference         16
                        note = misc_feature - n is a, c, g, or t
misc_difference         17
                        note = misc_feature - n is a, c, g, or t
misc_difference         18
                        note = misc_feature - n is a, c, g, or t
misc_difference         19
                        note = misc_feature - n is a, c, g, or t
misc_difference         20
                        note = misc_feature - n is a, c, g, or t
misc_difference         21
                        note = misc_feature - n is a, c, g, or t
misc_difference         22
                        note = misc_feature - n is a, c, g, or t
misc_difference         23
                        note = misc_feature - n is a, c, g, or t
SEQUENCE: 4
cgcgctgcat acttgnnnnn nnncccatga tcgtccga                               38

SEQ ID NO: 5            moltype = DNA  length = 30
FEATURE                 Location/Qualifiers
source                  1..30
                        mol_type = other DNA
                        organism = synthetic construct
                        note = BC_0058_S2-S3
SEQUENCE: 5
caagtatgca gcgcgggaa gcacgtggat                                         30

SEQ ID NO: 6            moltype = DNA  length = 38
FEATURE                 Location/Qualifiers
source                  1..38
```

```
                            mol_type = other DNA
                            organism = synthetic construct
                            note = Round 2 barcodes
misc_difference             16
                            note = misc_feature - n is a, c, g, or t
misc_difference             17
                            note = misc_feature - n is a, c, g, or t
misc_difference             18
                            note = misc_feature - n is a, c, g, or t
misc_difference             19
                            note = misc_feature - n is a, c, g, or t
misc_difference             20
                            note = misc_feature - n is a, c, g, or t
misc_difference             21
                            note = misc_feature - n is a, c, g, or t
misc_difference             22
                            note = misc_feature - n is a, c, g, or t
misc_difference             23
                            note = misc_feature - n is a, c, g, or t
SEQUENCE: 6
catcggcgta cgactnnnnn nnnatccacg tgcttccc                              38

SEQ ID NO: 7                moltype = DNA   length = 30
FEATURE                     Location/Qualifiers
source                      1..30
                            mol_type = other DNA
                            organism = synthetic construct
                            note = BC_0060_S4-S5
SEQUENCE: 7
agtcgtacgc cgatgcgaaa catcggccac                                       30

SEQ ID NO: 8                moltype = DNA   length = 55
FEATURE                     Location/Qualifiers
source                      1..55
                            mol_type = other DNA
                            organism = synthetic construct
                            note = Round 3 barcodes
misc_difference             23
                            note = misc_feature - n is a, c, g, or t
misc_difference             24
                            note = misc_feature - n is a, c, g, or t
misc_difference             25
                            note = misc_feature - n is a, c, g, or t
misc_difference             26
                            note = misc_feature - n is a, c, g, or t
misc_difference             27
                            note = misc_feature - n is a, c, g, or t
misc_difference             28
                            note = misc_feature - n is a, c, g, or t
misc_difference             29
                            note = misc_feature - n is a, c, g, or t
misc_difference             30
                            note = misc_feature - n is a, c, g, or t
misc_difference             31
                            note = misc_feature - n is a, c, g, or t
misc_difference             32
                            note = misc_feature - n is a, c, g, or t
misc_difference             33
                            note = misc_feature - n is a, c, g, or t
misc_difference             34
                            note = misc_feature - n is a, c, g, or t
misc_difference             35
                            note = misc_feature - n is a, c, g, or t
misc_difference             36
                            note = misc_feature - n is a, c, g, or t
misc_difference             37
                            note = misc_feature - n is a, c, g, or t
misc_difference             38
                            note = misc_feature - n is a, c, g, or t
misc_difference             39
                            note = misc_feature - n is a, c, g, or t
misc_difference             40
                            note = misc_feature - n is a, c, g, or t
SEQUENCE: 8
cagacgtgtg ctcttccgat ctnnnnnnnn nnnnnnnnnn gtggccgatg tttcg           55

SEQ ID NO: 9                moltype = DNA   length = 191
FEATURE                     Location/Qualifiers
source                      1..191
```

|                   |                                                                                                          |
|-------------------|----------------------------------------------------------------------------------------------------------|
|                   | mol_type = other DNA<br>organism = synthetic construct<br>note = Stop ligation oligos, top strand        |
| misc_difference   | 1                                                                                                        |
|                   | note = misc_feature - n is a, c, g, or t                                                                 |
| misc_difference   | 2                                                                                                        |
|                   | note = misc_feature - n is a, c, g, or t                                                                 |
| misc_difference   | 3                                                                                                        |
|                   | note = misc_feature - n is a, c, g, or t                                                                 |
| misc_difference   | 4                                                                                                        |
|                   | note = misc_feature - n is a, c, g, or t                                                                 |
| misc_difference   | 5                                                                                                        |
|                   | note = misc_feature - n is a, c, g, or t                                                                 |
| misc_difference   | 6                                                                                                        |
|                   | note = misc_feature - n is a, c, g, or t                                                                 |
| misc_difference   | 7                                                                                                        |
|                   | note = misc_feature - n is a, c, g, or t                                                                 |
| misc_difference   | 8                                                                                                        |
|                   | note = misc_feature - n is a, c, g, or t                                                                 |
| misc_difference   | 9                                                                                                        |
|                   | note = misc_feature - n is a, c, g, or t                                                                 |
| misc_difference   | 10                                                                                                       |
|                   | note = misc_feature - n is a, c, g, or t                                                                 |
| misc_difference   | 11                                                                                                       |
|                   | note = misc_feature - n is a, c, g, or t                                                                 |
| misc_difference   | 12                                                                                                       |
|                   | note = misc_feature - n is a, c, g, or t                                                                 |
| misc_difference   | 13                                                                                                       |
|                   | note = misc_feature - n is a, c, g, or t                                                                 |
| misc_difference   | 14                                                                                                       |
|                   | note = misc_feature - n is a, c, g, or t                                                                 |
| misc_difference   | 15                                                                                                       |
|                   | note = misc_feature - n is a, c, g, or t                                                                 |
| misc_difference   | 16                                                                                                       |
|                   | note = misc_feature - n is a, c, g, or t                                                                 |
| misc_difference   | 17                                                                                                       |
|                   | note = misc_feature - n is a, c, g, or t                                                                 |
| misc_difference   | 18                                                                                                       |
|                   | note = misc_feature - n is a, c, g, or t                                                                 |
| misc_difference   | 19                                                                                                       |
|                   | note = misc_feature - n is a, c, g, or t                                                                 |
| misc_difference   | 20                                                                                                       |
|                   | note = misc_feature - n is a, c, g, or t                                                                 |
| misc_difference   | 21                                                                                                       |
|                   | note = misc_feature - n is a, c, g, or t                                                                 |
| misc_difference   | 22                                                                                                       |
|                   | note = misc_feature - n is a, c, g, or t                                                                 |
| misc_difference   | 23                                                                                                       |
|                   | note = misc_feature - n is a, c, g, or t                                                                 |
| misc_difference   | 24                                                                                                       |
|                   | note = misc_feature - n is a, c, g, or t                                                                 |
| misc_difference   | 25                                                                                                       |
|                   | note = misc_feature - n is a, c, g, or t                                                                 |
| misc_difference   | 26                                                                                                       |
|                   | note = misc_feature - n is a, c, g, or t                                                                 |
| misc_difference   | 27                                                                                                       |
|                   | note = misc_feature - n is a, c, g, or t                                                                 |
| misc_difference   | 28                                                                                                       |
|                   | note = misc_feature - n is a, c, g, or t                                                                 |
| misc_difference   | 29                                                                                                       |
|                   | note = misc_feature - n is a, c, g, or t                                                                 |
| misc_difference   | 76                                                                                                       |
|                   | note = misc_feature - n is a, c, g, or t                                                                 |
| misc_difference   | 77                                                                                                       |
|                   | note = misc_feature - n is a, c, g, or t                                                                 |
| misc_difference   | 78                                                                                                       |
|                   | note = misc_feature - n is a, c, g, or t                                                                 |
| misc_difference   | 79                                                                                                       |
|                   | note = misc_feature - n is a, c, g, or t                                                                 |
| misc_difference   | 80                                                                                                       |
|                   | note = misc_feature - n is a, c, g, or t                                                                 |
| misc_difference   | 81                                                                                                       |
|                   | note = misc_feature - n is a, c, g, or t                                                                 |
| misc_difference   | 82                                                                                                       |
|                   | note = misc_feature - n is a, c, g, or t                                                                 |
| misc_difference   | 83                                                                                                       |
|                   | note = misc_feature - n is a, c, g, or t                                                                 |
| misc_difference   | 114                                                                                                      |
|                   | note = misc_feature - n is a, c, g, or t                                                                 |

-continued

```
misc_difference      115
                     note = misc_feature - n is a, c, g, or t
misc_difference      116
                     note = misc_feature - n is a, c, g, or t
misc_difference      117
                     note = misc_feature - n is a, c, g, or t
misc_difference      118
                     note = misc_feature - n is a, c, g, or t
misc_difference      119
                     note = misc_feature - n is a, c, g, or t
misc_difference      120
                     note = misc_feature - n is a, c, g, or t
misc_difference      121
                     note = misc_feature - n is a, c, g, or t
misc_difference      152
                     note = misc_feature - n is a, c, g, or t
misc_difference      153
                     note = misc_feature - n is a, c, g, or t
misc_difference      154
                     note = misc_feature - n is a, c, g, or t
misc_difference      155
                     note = misc_feature - n is a, c, g, or t
misc_difference      156
                     note = misc_feature - n is a, c, g, or t
misc_difference      157
                     note = misc_feature - n is a, c, g, or t
misc_difference      158
                     note = misc_feature - n is a, c, g, or t
misc_difference      159
                     note = misc_feature - n is a, c, g, or t
misc_difference      160
                     note = misc_feature - n is a, c, g, or t
misc_difference      161
                     note = misc_feature - n is a, c, g, or t
misc_difference      162
                     note = misc_feature - n is a, c, g, or t
misc_difference      163
                     note = misc_feature - n is a, c, g, or t
misc_difference      164
                     note = misc_feature - n is a, c, g, or t
misc_difference      165
                     note = misc_feature - n is a, c, g, or t
misc_difference      166
                     note = misc_feature - n is a, c, g, or t
misc_difference      167
                     note = misc_feature - n is a, c, g, or t
misc_difference      168
                     note = misc_feature - n is a, c, g, or t
misc_difference      169
                     note = misc_feature - n is a, c, g, or t
SEQUENCE: 9
nnnnnnnnnn nnnnnnnnnn nnnnnnnnnb aaaaaaaaaa aaaaacgaat gctctggcct    60
tcggacgatc atgggnnnnn nnncaagtat gcagcgcggg gaagcacgtg gatnnnnnnn   120
nagtcgtacg ccgatgcgaa acatcggcca cnnnnnnnnn nnnnnnnnna gatcggaaga   180
gcacacgtct g                                                       191

SEQ ID NO: 10        moltype = DNA  length = 191
FEATURE              Location/Qualifiers
source               1..191
                     mol_type = other DNA
                     organism = synthetic construct
                     note = Stop ligation oligos, bottom strand
misc_difference      23
                     note = misc_feature - n is a, c, g, or t
misc_difference      24
                     note = misc_feature - n is a, c, g, or t
misc_difference      25
                     note = misc_feature - n is a, c, g, or t
misc_difference      26
                     note = misc_feature - n is a, c, g, or t
misc_difference      27
                     note = misc_feature - n is a, c, g, or t
misc_difference      28
                     note = misc_feature - n is a, c, g, or t
misc_difference      29
                     note = misc_feature - n is a, c, g, or t
misc_difference      30
                     note = misc_feature - n is a, c, g, or t
misc_difference      31
```

| | | |
|---|---|---|
| | | note = misc_feature - n is a, c, g, or t |
| misc_difference | 32 | |
| | | note = misc_feature - n is a, c, g, or t |
| misc_difference | 33 | |
| | | note = misc_feature - n is a, c, g, or t |
| misc_difference | 34 | |
| | | note = misc_feature - n is a, c, g, or t |
| misc_difference | 35 | |
| | | note = misc_feature - n is a, c, g, or t |
| misc_difference | 36 | |
| | | note = misc_feature - n is a, c, g, or t |
| misc_difference | 37 | |
| | | note = misc_feature - n is a, c, g, or t |
| misc_difference | 38 | |
| | | note = misc_feature - n is a, c, g, or t |
| misc_difference | 39 | |
| | | note = misc_feature - n is a, c, g, or t |
| misc_difference | 40 | |
| | | note = misc_feature - n is a, c, g, or t |
| misc_difference | 71 | |
| | | note = misc_feature - n is a, c, g, or t |
| misc_difference | 72 | |
| | | note = misc_feature - n is a, c, g, or t |
| misc_difference | 73 | |
| | | note = misc_feature - n is a, c, g, or t |
| misc_difference | 74 | |
| | | note = misc_feature - n is a, c, g, or t |
| misc_difference | 75 | |
| | | note = misc_feature - n is a, c, g, or t |
| misc_difference | 76 | |
| | | note = misc_feature - n is a, c, g, or t |
| misc_difference | 77 | |
| | | note = misc_feature - n is a, c, g, or t |
| misc_difference | 78 | |
| | | note = misc_feature - n is a, c, g, or t |
| misc_difference | 109 | |
| | | note = misc_feature - n is a, c, g, or t |
| misc_difference | 110 | |
| | | note = misc_feature - n is a, c, g, or t |
| misc_difference | 111 | |
| | | note = misc_feature - n is a, c, g, or t |
| misc_difference | 112 | |
| | | note = misc_feature - n is a, c, g, or t |
| misc_difference | 113 | |
| | | note = misc_feature - n is a, c, g, or t |
| misc_difference | 114 | |
| | | note = misc_feature - n is a, c, g, or t |
| misc_difference | 115 | |
| | | note = misc_feature - n is a, c, g, or t |
| misc_difference | 116 | |
| | | note = misc_feature - n is a, c, g, or t |
| misc_difference | 163 | |
| | | note = misc_feature - n is a, c, g, or t |
| misc_difference | 164 | |
| | | note = misc_feature - n is a, c, g, or t |
| misc_difference | 165 | |
| | | note = misc_feature - n is a, c, g, or t |
| misc_difference | 166 | |
| | | note = misc_feature - n is a, c, g, or t |
| misc_difference | 167 | |
| | | note = misc_feature - n is a, c, g, or t |
| misc_difference | 168 | |
| | | note = misc_feature - n is a, c, g, or t |
| misc_difference | 169 | |
| | | note = misc_feature - n is a, c, g, or t |
| misc_difference | 170 | |
| | | note = misc_feature - n is a, c, g, or t |
| misc_difference | 171 | |
| | | note = misc_feature - n is a, c, g, or t |
| misc_difference | 172 | |
| | | note = misc_feature - n is a, c, g, or t |
| misc_difference | 173 | |
| | | note = misc_feature - n is a, c, g, or t |
| misc_difference | 174 | |
| | | note = misc_feature - n is a, c, g, or t |
| misc_difference | 175 | |
| | | note = misc_feature - n is a, c, g, or t |
| misc_difference | 176 | |
| | | note = misc_feature - n is a, c, g, or t |

| | |
|---|---|
| misc_difference | 177 |
| | note = misc_feature - n is a, c, g, or t |
| misc_difference | 178 |
| | note = misc_feature - n is a, c, g, or t |
| misc_difference | 179 |
| | note = misc_feature - n is a, c, g, or t |
| misc_difference | 180 |
| | note = misc_feature - n is a, c, g, or t |
| misc_difference | 181 |
| | note = misc_feature - n is a, c, g, or t |
| misc_difference | 182 |
| | note = misc_feature - n is a, c, g, or t |
| misc_difference | 183 |
| | note = misc_feature - n is a, c, g, or t |
| misc_difference | 184 |
| | note = misc_feature - n is a, c, g, or t |
| misc_difference | 185 |
| | note = misc_feature - n is a, c, g, or t |
| misc_difference | 186 |
| | note = misc_feature - n is a, c, g, or t |
| misc_difference | 187 |
| | note = misc_feature - n is a, c, g, or t |
| misc_difference | 188 |
| | note = misc_feature - n is a, c, g, or t |
| misc_difference | 189 |
| | note = misc_feature - n is a, c, g, or t |
| misc_difference | 190 |
| | note = misc_feature - n is a, c, g, or t |
| misc_difference | 191 |
| | note = misc_feature - n is a, c, g, or t |

```
SEQUENCE: 10
cagacgtgtg ctcttccgat ctnnnnnnnn nnnnnnnnnn gtggccgatg tttcgcatcg   60
gcgtacgact nnnnnnnnat ccacgtgctt ccccgcgctg catacttgnn nnnnnccca   120
tgatcgtccg aaggccagag cattcgtttt tttttttttt tvnnnnnnnn nnnnnnnnnn  180
nnnnnnnnn n                                                       191
```

| | |
|---|---|
| SEQ ID NO: 11 | moltype = DNA   length = 214 |
| FEATURE | Location/Qualifiers |
| source | 1..214 |
| | mol_type = other DNA |
| | organism = synthetic construct |
| | note = 3' adapter ligation |
| misc_difference | 24 |
| | note = misc_feature - n is a, c, g, or t |
| misc_difference | 25 |
| | note = misc_feature - n is a, c, g, or t |
| misc_difference | 26 |
| | note = misc_feature - n is a, c, g, or t |
| misc_difference | 27 |
| | note = misc_feature - n is a, c, g, or t |
| misc_difference | 28 |
| | note = misc_feature - n is a, c, g, or t |
| misc_difference | 29 |
| | note = misc_feature - n is a, c, g, or t |
| misc_difference | 30 |
| | note = misc_feature - n is a, c, g, or t |
| misc_difference | 31 |
| | note = misc_feature - n is a, c, g, or t |
| misc_difference | 32 |
| | note = misc_feature - n is a, c, g, or t |
| misc_difference | 33 |
| | note = misc_feature - n is a, c, g, or t |
| misc_difference | 34 |
| | note = misc_feature - n is a, c, g, or t |
| misc_difference | 35 |
| | note = misc_feature - n is a, c, g, or t |
| misc_difference | 36 |
| | note = misc_feature - n is a, c, g, or t |
| misc_difference | 37 |
| | note = misc_feature - n is a, c, g, or t |
| misc_difference | 38 |
| | note = misc_feature - n is a, c, g, or t |
| misc_difference | 39 |
| | note = misc_feature - n is a, c, g, or t |
| misc_difference | 40 |
| | note = misc_feature - n is a, c, g, or t |
| misc_difference | 41 |
| | note = misc_feature - n is a, c, g, or t |
| misc_difference | 42 |

| | | |
|---|---|---|
| misc_difference | 43 | note = misc_feature - n is a, c, g, or t |
| misc_difference | 44 | note = misc_feature - n is a, c, g, or t |
| misc_difference | 45 | note = misc_feature - n is a, c, g, or t |
| misc_difference | 46 | note = misc_feature - n is a, c, g, or t |
| misc_difference | 47 | note = misc_feature - n is a, c, g, or t |
| misc_difference | 48 | note = misc_feature - n is a, c, g, or t |
| misc_difference | 49 | note = misc_feature - n is a, c, g, or t |
| misc_difference | 50 | note = misc_feature - n is a, c, g, or t |
| misc_difference | 51 | note = misc_feature - n is a, c, g, or t |
| misc_difference | 52 | note = misc_feature - n is a, c, g, or t |
| misc_difference | 99 | note = misc_feature - n is a, c, g, or t |
| misc_difference | 100 | note = misc_feature - n is a, c, g, or t |
| misc_difference | 101 | note = misc_feature - n is a, c, g, or t |
| misc_difference | 102 | note = misc_feature - n is a, c, g, or t |
| misc_difference | 103 | note = misc_feature - n is a, c, g, or t |
| misc_difference | 104 | note = misc_feature - n is a, c, g, or t |
| misc_difference | 105 | note = misc_feature - n is a, c, g, or t |
| misc_difference | 106 | note = misc_feature - n is a, c, g, or t |
| misc_difference | 137 | note = misc_feature - n is a, c, g, or t |
| misc_difference | 138 | note = misc_feature - n is a, c, g, or t |
| misc_difference | 139 | note = misc_feature - n is a, c, g, or t |
| misc_difference | 140 | note = misc_feature - n is a, c, g, or t |
| misc_difference | 141 | note = misc_feature - n is a, c, g, or t |
| misc_difference | 142 | note = misc_feature - n is a, c, g, or t |
| misc_difference | 143 | note = misc_feature - n is a, c, g, or t |
| misc_difference | 144 | note = misc_feature - n is a, c, g, or t |
| misc_difference | 175 | note = misc_feature - n is a, c, g, or t |
| misc_difference | 176 | note = misc_feature - n is a, c, g, or t |
| misc_difference | 177 | note = misc_feature - n is a, c, g, or t |
| misc_difference | 178 | note = misc_feature - n is a, c, g, or t |
| misc_difference | 179 | note = misc_feature - n is a, c, g, or t |
| misc_difference | 180 | note = misc_feature - n is a, c, g, or t |
| misc_difference | 181 | note = misc_feature - n is a, c, g, or t |
| misc_difference | 182 | note = misc_feature - n is a, c, g, or t |
| misc_difference | 183 | note = misc_feature - n is a, c, g, or t |
| misc_difference | 184 | note = misc_feature - n is a, c, g, or t |
| misc_difference | 185 | note = misc_feature - n is a, c, g, or t |
| misc_difference | 186 | note = misc_feature - n is a, c, g, or t |
| misc_difference | 187 | note = misc_feature - n is a, c, g, or t |

```
misc_difference        188
                       note = misc_feature - n is a, c, g, or t
misc_difference        189
                       note = misc_feature - n is a, c, g, or t
misc_difference        190
                       note = misc_feature - n is a, c, g, or t
misc_difference        191
                       note = misc_feature - n is a, c, g, or t
misc_difference        192
                       note = misc_feature - n is a, c, g, or t
SEQUENCE: 11
ggatgtgctg cgagaaggct agannnnnnn nnnnnnnnnn nnvttttttt   60
ttttttttgc ttacgagacc ggaagcctgc tagtacccnn nnnnnngttc atacgtcgcg  120
ccccttcgtg cacctannnn nnnntcagca tgcggctacg ctttgtagcc ggtgnnnnnn  180
nnnnnnnnnn nntctagcct tctcgtgtgc agac                             214

SEQ ID NO: 12          moltype = DNA  length = 214
FEATURE                Location/Qualifiers
source                 1..214
                       mol_type = other DNA
                       organism = synthetic construct
                       note = PCR #1, top strand
misc_difference        24
                       note = misc_feature - n is a, c, g, or t
misc_difference        25
                       note = misc_feature - n is a, c, g, or t
misc_difference        26
                       note = misc_feature - n is a, c, g, or t
misc_difference        27
                       note = misc_feature - n is a, c, g, or t
misc_difference        28
                       note = misc_feature - n is a, c, g, or t
misc_difference        29
                       note = misc_feature - n is a, c, g, or t
misc_difference        30
                       note = misc_feature - n is a, c, g, or t
misc_difference        31
                       note = misc_feature - n is a, c, g, or t
misc_difference        32
                       note = misc_feature - n is a, c, g, or t
misc_difference        33
                       note = misc_feature - n is a, c, g, or t
misc_difference        34
                       note = misc_feature - n is a, c, g, or t
misc_difference        35
                       note = misc_feature - n is a, c, g, or t
misc_difference        36
                       note = misc_feature - n is a, c, g, or t
misc_difference        37
                       note = misc_feature - n is a, c, g, or t
misc_difference        38
                       note = misc_feature - n is a, c, g, or t
misc_difference        39
                       note = misc_feature - n is a, c, g, or t
misc_difference        40
                       note = misc_feature - n is a, c, g, or t
misc_difference        41
                       note = misc_feature - n is a, c, g, or t
misc_difference        42
                       note = misc_feature - n is a, c, g, or t
misc_difference        43
                       note = misc_feature - n is a, c, g, or t
misc_difference        44
                       note = misc_feature - n is a, c, g, or t
misc_difference        45
                       note = misc_feature - n is a, c, g, or t
misc_difference        46
                       note = misc_feature - n is a, c, g, or t
misc_difference        47
                       note = misc_feature - n is a, c, g, or t
misc_difference        48
                       note = misc_feature - n is a, c, g, or t
misc_difference        49
                       note = misc_feature - n is a, c, g, or t
misc_difference        50
                       note = misc_feature - n is a, c, g, or t
misc_difference        51
                       note = misc_feature - n is a, c, g, or t
misc_difference        52
```

| | | |
|---|---|---|
| misc_difference | 99 | note = misc_feature - n is a, c, g, or t |
| misc_difference | 100 | note = misc_feature - n is a, c, g, or t |
| misc_difference | 101 | note = misc_feature - n is a, c, g, or t |
| misc_difference | 102 | note = misc_feature - n is a, c, g, or t |
| misc_difference | 103 | note = misc_feature - n is a, c, g, or t |
| misc_difference | 104 | note = misc_feature - n is a, c, g, or t |
| misc_difference | 105 | note = misc_feature - n is a, c, g, or t |
| misc_difference | 106 | note = misc_feature - n is a, c, g, or t |
| misc_difference | 137 | note = misc_feature - n is a, c, g, or t |
| misc_difference | 138 | note = misc_feature - n is a, c, g, or t |
| misc_difference | 139 | note = misc_feature - n is a, c, g, or t |
| misc_difference | 140 | note = misc_feature - n is a, c, g, or t |
| misc_difference | 141 | note = misc_feature - n is a, c, g, or t |
| misc_difference | 142 | note = misc_feature - n is a, c, g, or t |
| misc_difference | 143 | note = misc_feature - n is a, c, g, or t |
| misc_difference | 144 | note = misc_feature - n is a, c, g, or t |
| misc_difference | 175 | note = misc_feature - n is a, c, g, or t |
| misc_difference | 176 | note = misc_feature - n is a, c, g, or t |
| misc_difference | 177 | note = misc_feature - n is a, c, g, or t |
| misc_difference | 178 | note = misc_feature - n is a, c, g, or t |
| misc_difference | 179 | note = misc_feature - n is a, c, g, or t |
| misc_difference | 180 | note = misc_feature - n is a, c, g, or t |
| misc_difference | 181 | note = misc_feature - n is a, c, g, or t |
| misc_difference | 182 | note = misc_feature - n is a, c, g, or t |
| misc_difference | 183 | note = misc_feature - n is a, c, g, or t |
| misc_difference | 184 | note = misc_feature - n is a, c, g, or t |
| misc_difference | 185 | note = misc_feature - n is a, c, g, or t |
| misc_difference | 186 | note = misc_feature - n is a, c, g, or t |
| misc_difference | 187 | note = misc_feature - n is a, c, g, or t |
| misc_difference | 188 | note = misc_feature - n is a, c, g, or t |
| misc_difference | 189 | note = misc_feature - n is a, c, g, or t |
| misc_difference | 190 | note = misc_feature - n is a, c, g, or t |
| misc_difference | 191 | note = misc_feature - n is a, c, g, or t |
| misc_difference | 192 | note = misc_feature - n is a, c, g, or t |

```
SEQUENCE: 12
cctacacgac gctcttccga tctnnnnnnn nnnnnnnnnn nnnnnnnnnn nnbaaaaaaa   60
aaaaaaaacg aatgctctgg ccttcggacg atcatgggnn nnnnnncaag tatgcagcgc  120
ggggaagcac gtggatnnnn nnnnagtcgt acgccgatgc gaaacatcgg ccacnnnnnn  180
nnnnnnnnnn nnagatcgga agagcacacg tctg                              214
```

| | | |
|---|---|---|
| SEQ ID NO: 13 | | moltype = DNA   length = 214 |
| FEATURE | | Location/Qualifiers |
| source | | 1..214 |
| | | mol_type = other DNA |

-continued

| | organism = synthetic construct<br>note = PCR #1, bottom strand |
|---|---|
| misc_difference | 23<br>note = misc_feature - n is a, c, g, or t |
| misc_difference | 24<br>note = misc_feature - n is a, c, g, or t |
| misc_difference | 25<br>note = misc_feature - n is a, c, g, or t |
| misc_difference | 26<br>note = misc_feature - n is a, c, g, or t |
| misc_difference | 27<br>note = misc_feature - n is a, c, g, or t |
| misc_difference | 28<br>note = misc_feature - n is a, c, g, or t |
| misc_difference | 29<br>note = misc_feature - n is a, c, g, or t |
| misc_difference | 30<br>note = misc_feature - n is a, c, g, or t |
| misc_difference | 31<br>note = misc_feature - n is a, c, g, or t |
| misc_difference | 32<br>note = misc_feature - n is a, c, g, or t |
| misc_difference | 33<br>note = misc_feature - n is a, c, g, or t |
| misc_difference | 34<br>note = misc_feature - n is a, c, g, or t |
| misc_difference | 35<br>note = misc_feature - n is a, c, g, or t |
| misc_difference | 36<br>note = misc_feature - n is a, c, g, or t |
| misc_difference | 37<br>note = misc_feature - n is a, c, g, or t |
| misc_difference | 38<br>note = misc_feature - n is a, c, g, or t |
| misc_difference | 39<br>note = misc_feature - n is a, c, g, or t |
| misc_difference | 40<br>note = misc_feature - n is a, c, g, or t |
| misc_difference | 71<br>note = misc_feature - n is a, c, g, or t |
| misc_difference | 72<br>note = misc_feature - n is a, c, g, or t |
| misc_difference | 73<br>note = misc_feature - n is a, c, g, or t |
| misc_difference | 74<br>note = misc_feature - n is a, c, g, or t |
| misc_difference | 75<br>note = misc_feature - n is a, c, g, or t |
| misc_difference | 76<br>note = misc_feature - n is a, c, g, or t |
| misc_difference | 77<br>note = misc_feature - n is a, c, g, or t |
| misc_difference | 78<br>note = misc_feature - n is a, c, g, or t |
| misc_difference | 109<br>note = misc_feature - n is a, c, g, or t |
| misc_difference | 110<br>note = misc_feature - n is a, c, g, or t |
| misc_difference | 111<br>note = misc_feature - n is a, c, g, or t |
| misc_difference | 112<br>note = misc_feature - n is a, c, g, or t |
| misc_difference | 113<br>note = misc_feature - n is a, c, g, or t |
| misc_difference | 114<br>note = misc_feature - n is a, c, g, or t |
| misc_difference | 115<br>note = misc_feature - n is a, c, g, or t |
| misc_difference | 116<br>note = misc_feature - n is a, c, g, or t |
| misc_difference | 163<br>note = misc_feature - n is a, c, g, or t |
| misc_difference | 164<br>note = misc_feature - n is a, c, g, or t |
| misc_difference | 165<br>note = misc_feature - n is a, c, g, or t |
| misc_difference | 166<br>note = misc_feature - n is a, c, g, or t |
| misc_difference | 167 |

| | | |
|---|---|---|
| misc_difference | 168 | note = misc_feature - n is a, c, g, or t |
| misc_difference | 169 | note = misc_feature - n is a, c, g, or t |
| misc_difference | 170 | note = misc_feature - n is a, c, g, or t |
| misc_difference | 171 | note = misc_feature - n is a, c, g, or t |
| misc_difference | 172 | note = misc_feature - n is a, c, g, or t |
| misc_difference | 173 | note = misc_feature - n is a, c, g, or t |
| misc_difference | 174 | note = misc_feature - n is a, c, g, or t |
| misc_difference | 175 | note = misc_feature - n is a, c, g, or t |
| misc_difference | 176 | note = misc_feature - n is a, c, g, or t |
| misc_difference | 177 | note = misc_feature - n is a, c, g, or t |
| misc_difference | 178 | note = misc_feature - n is a, c, g, or t |
| misc_difference | 179 | note = misc_feature - n is a, c, g, or t |
| misc_difference | 180 | note = misc_feature - n is a, c, g, or t |
| misc_difference | 181 | note = misc_feature - n is a, c, g, or t |
| misc_difference | 182 | note = misc_feature - n is a, c, g, or t |
| misc_difference | 183 | note = misc_feature - n is a, c, g, or t |
| misc_difference | 184 | note = misc_feature - n is a, c, g, or t |
| misc_difference | 185 | note = misc_feature - n is a, c, g, or t |
| misc_difference | 186 | note = misc_feature - n is a, c, g, or t |
| misc_difference | 187 | note = misc_feature - n is a, c, g, or t |
| misc_difference | 188 | note = misc_feature - n is a, c, g, or t |
| misc_difference | 189 | note = misc_feature - n is a, c, g, or t |
| misc_difference | 190 | note = misc_feature - n is a, c, g, or t |
| misc_difference | 191 | note = misc_feature - n is a, c, g, or t |

SEQUENCE: 13

```
cagacgtgtg ctcttccgat ctnnnnnnnn nnnnnnnnnn gtggccgatg tttcgcatcg   60
gcgtacgact nnnnnnnnat ccacgtgctt ccccgcgctg catacttgnn nnnnnnccca  120
tgatcgtccg aaggccagag cattcgtttt tttttttttt tvnnnnnnnn nnnnnnnnnn  180
nnnnnnnnnn nagatcggaa gagcgtcgtg tagg                              214
```

| | | |
|---|---|---|
| SEQ ID NO: 14 | moltype = DNA  length = 292 | |
| FEATURE | Location/Qualifiers | |
| source | 1..292 | |
| | mol_type = other DNA | |
| | organism = synthetic construct | |
| | note = PCR #1, top strand | |
| misc_difference | 59 | note = misc_feature - n is a, c, g, or t |
| misc_difference | 60 | note = misc_feature - n is a, c, g, or t |
| misc_difference | 61 | note = misc_feature - n is a, c, g, or t |
| misc_difference | 62 | note = misc_feature - n is a, c, g, or t |
| misc_difference | 63 | note = misc_feature - n is a, c, g, or t |
| misc_difference | 64 | note = misc_feature - n is a, c, g, or t |
| misc_difference | 65 | note = misc_feature - n is a, c, g, or t |
| misc_difference | 66 | note = misc_feature - n is a, c, g, or t |
| misc_difference | 67 | note = misc_feature - n is a, c, g, or t |

-continued

| | |
|---|---|
| misc_difference | 68 |
| | note = misc_feature - n is a, c, g, or t |
| misc_difference | 69 |
| | note = misc_feature - n is a, c, g, or t |
| misc_difference | 70 |
| | note = misc_feature - n is a, c, g, or t |
| misc_difference | 71 |
| | note = misc_feature - n is a, c, g, or t |
| misc_difference | 72 |
| | note = misc_feature - n is a, c, g, or t |
| misc_difference | 73 |
| | note = misc_feature - n is a, c, g, or t |
| misc_difference | 74 |
| | note = misc_feature - n is a, c, g, or t |
| misc_difference | 75 |
| | note = misc_feature - n is a, c, g, or t |
| misc_difference | 76 |
| | note = misc_feature - n is a, c, g, or t |
| misc_difference | 77 |
| | note = misc_feature - n is a, c, g, or t |
| misc_difference | 78 |
| | note = misc_feature - n is a, c, g, or t |
| misc_difference | 79 |
| | note = misc_feature - n is a, c, g, or t |
| misc_difference | 80 |
| | note = misc_feature - n is a, c, g, or t |
| misc_difference | 81 |
| | note = misc_feature - n is a, c, g, or t |
| misc_difference | 82 |
| | note = misc_feature - n is a, c, g, or t |
| misc_difference | 83 |
| | note = misc_feature - n is a, c, g, or t |
| misc_difference | 84 |
| | note = misc_feature - n is a, c, g, or t |
| misc_difference | 85 |
| | note = misc_feature - n is a, c, g, or t |
| misc_difference | 86 |
| | note = misc_feature - n is a, c, g, or t |
| misc_difference | 87 |
| | note = misc_feature - n is a, c, g, or t |
| misc_difference | 88 |
| | note = misc_feature - n is a, c, g, or t |
| misc_difference | 135 |
| | note = misc_feature - n is a, c, g, or t |
| misc_difference | 136 |
| | note = misc_feature - n is a, c, g, or t |
| misc_difference | 137 |
| | note = misc_feature - n is a, c, g, or t |
| misc_difference | 138 |
| | note = misc_feature - n is a, c, g, or t |
| misc_difference | 139 |
| | note = misc_feature - n is a, c, g, or t |
| misc_difference | 140 |
| | note = misc_feature - n is a, c, g, or t |
| misc_difference | 141 |
| | note = misc_feature - n is a, c, g, or t |
| misc_difference | 142 |
| | note = misc_feature - n is a, c, g, or t |
| misc_difference | 173 |
| | note = misc_feature - n is a, c, g, or t |
| misc_difference | 174 |
| | note = misc_feature - n is a, c, g, or t |
| misc_difference | 175 |
| | note = misc_feature - n is a, c, g, or t |
| misc_difference | 176 |
| | note = misc_feature - n is a, c, g, or t |
| misc_difference | 177 |
| | note = misc_feature - n is a, c, g, or t |
| misc_difference | 178 |
| | note = misc_feature - n is a, c, g, or t |
| misc_difference | 179 |
| | note = misc_feature - n is a, c, g, or t |
| misc_difference | 180 |
| | note = misc_feature - n is a, c, g, or t |
| misc_difference | 211 |
| | note = misc_feature - n is a, c, g, or t |
| misc_difference | 212 |
| | note = misc_feature - n is a, c, g, or t |
| misc_difference | 213 |

|  |  |
|---|---|
| misc_difference | 214 |
|  | note = misc_feature - n is a, c, g, or t |
| misc_difference | 215 |
|  | note = misc_feature - n is a, c, g, or t |
| misc_difference | 216 |
|  | note = misc_feature - n is a, c, g, or t |
| misc_difference | 217 |
|  | note = misc_feature - n is a, c, g, or t |
| misc_difference | 218 |
|  | note = misc_feature - n is a, c, g, or t |
| misc_difference | 219 |
|  | note = misc_feature - n is a, c, g, or t |
| misc_difference | 220 |
|  | note = misc_feature - n is a, c, g, or t |
| misc_difference | 221 |
|  | note = misc_feature - n is a, c, g, or t |
| misc_difference | 222 |
|  | note = misc_feature - n is a, c, g, or t |
| misc_difference | 223 |
|  | note = misc_feature - n is a, c, g, or t |
| misc_difference | 224 |
|  | note = misc_feature - n is a, c, g, or t |
| misc_difference | 225 |
|  | note = misc_feature - n is a, c, g, or t |
| misc_difference | 226 |
|  | note = misc_feature - n is a, c, g, or t |
| misc_difference | 227 |
|  | note = misc_feature - n is a, c, g, or t |
| misc_difference | 228 |
|  | note = misc_feature - n is a, c, g, or t |

SEQUENCE: 14

```
aatgatacgg cgaccaccga gatctacact ctttccctac acgacgctct tccgatctnn    60
nnnnnnnnnn nnnnnnnnnn nnnnnnnnba aaaaaaaaaa aaaacgaatg ctctggcctt   120
cggacgatca tgggnnnnnn nncaagtatg cagcgcgggg aagcacgtgg atnnnnnnnn   180
agtcgtacgc cgatgcgaaa catcggccac nnnnnnnnnn nnnnnnnnag atcggaagag   240
cacacgtctg aactccagtc acgatctgat ctcgtatgcc gtcttctgct tg           292
```

|  |  |
|---|---|
| SEQ ID NO: 15 | moltype = DNA  length = 292 |
| FEATURE | Location/Qualifiers |
| source | 1..292 |
|  | mol_type = other DNA |
|  | organism = synthetic construct |
|  | note = PCR #2, bottom strand |
| misc_difference | 65 |
|  | note = misc_feature - n is a, c, g, or t |
| misc_difference | 66 |
|  | note = misc_feature - n is a, c, g, or t |
| misc_difference | 67 |
|  | note = misc_feature - n is a, c, g, or t |
| misc_difference | 68 |
|  | note = misc_feature - n is a, c, g, or t |
| misc_difference | 69 |
|  | note = misc_feature - n is a, c, g, or t |
| misc_difference | 70 |
|  | note = misc_feature - n is a, c, g, or t |
| misc_difference | 71 |
|  | note = misc_feature - n is a, c, g, or t |
| misc_difference | 72 |
|  | note = misc_feature - n is a, c, g, or t |
| misc_difference | 73 |
|  | note = misc_feature - n is a, c, g, or t |
| misc_difference | 74 |
|  | note = misc_feature - n is a, c, g, or t |
| misc_difference | 75 |
|  | note = misc_feature - n is a, c, g, or t |
| misc_difference | 76 |
|  | note = misc_feature - n is a, c, g, or t |
| misc_difference | 77 |
|  | note = misc_feature - n is a, c, g, or t |
| misc_difference | 78 |
|  | note = misc_feature - n is a, c, g, or t |
| misc_difference | 79 |
|  | note = misc_feature - n is a, c, g, or t |
| misc_difference | 80 |
|  | note = misc_feature - n is a, c, g, or t |
| misc_difference | 81 |
|  | note = misc_feature - n is a, c, g, or t |
| misc_difference | 82 |

-continued

| | |
|---|---|
| misc_difference | note = misc_feature - n is a, c, g, or t 113 |
| misc_difference | note = misc_feature - n is a, c, g, or t 114 |
| misc_difference | note = misc_feature - n is a, c, g, or t 115 |
| misc_difference | note = misc_feature - n is a, c, g, or t 116 |
| misc_difference | note = misc_feature - n is a, c, g, or t 117 |
| misc_difference | note = misc_feature - n is a, c, g, or t 118 |
| misc_difference | note = misc_feature - n is a, c, g, or t 119 |
| misc_difference | note = misc_feature - n is a, c, g, or t 120 |
| misc_difference | note = misc_feature - n is a, c, g, or t 151 |
| misc_difference | note = misc_feature - n is a, c, g, or t 152 |
| misc_difference | note = misc_feature - n is a, c, g, or t 153 |
| misc_difference | note = misc_feature - n is a, c, g, or t 154 |
| misc_difference | note = misc_feature - n is a, c, g, or t 155 |
| misc_difference | note = misc_feature - n is a, c, g, or t 156 |
| misc_difference | note = misc_feature - n is a, c, g, or t 157 |
| misc_difference | note = misc_feature - n is a, c, g, or t 158 |
| misc_difference | note = misc_feature - n is a, c, g, or t 205 |
| misc_difference | note = misc_feature - n is a, c, g, or t 206 |
| misc_difference | note = misc_feature - n is a, c, g, or t 207 |
| misc_difference | note = misc_feature - n is a, c, g, or t 208 |
| misc_difference | note = misc_feature - n is a, c, g, or t 209 |
| misc_difference | note = misc_feature - n is a, c, g, or t 210 |
| misc_difference | note = misc_feature - n is a, c, g, or t 211 |
| misc_difference | note = misc_feature - n is a, c, g, or t 212 |
| misc_difference | note = misc_feature - n is a, c, g, or t 213 |
| misc_difference | note = misc_feature - n is a, c, g, or t 214 |
| misc_difference | note = misc_feature - n is a, c, g, or t 215 |
| misc_difference | note = misc_feature - n is a, c, g, or t 216 |
| misc_difference | note = misc_feature - n is a, c, g, or t 217 |
| misc_difference | note = misc_feature - n is a, c, g, or t 218 |
| misc_difference | note = misc_feature - n is a, c, g, or t 219 |
| misc_difference | note = misc_feature - n is a, c, g, or t 220 |
| misc_difference | note = misc_feature - n is a, c, g, or t 221 |
| misc_difference | note = misc_feature - n is a, c, g, or t 222 |
| misc_difference | note = misc_feature - n is a, c, g, or t 223 |
| misc_difference | note = misc_feature - n is a, c, g, or t 224 |
| misc_difference | note = misc_feature - n is a, c, g, or t 225 |
| misc_difference | note = misc_feature - n is a, c, g, or t 226 |
| misc_difference | note = misc_feature - n is a, c, g, or t 227 |
| | note = misc_feature - n is a, c, g, or t |

```
                                -continued
misc_difference         228
                        note = misc_feature - n is a, c, g, or t
misc_difference         229
                        note = misc_feature - n is a, c, g, or t
misc_difference         230
                        note = misc_feature - n is a, c, g, or t
misc_difference         231
                        note = misc_feature - n is a, c, g, or t
misc_difference         232
                        note = misc_feature - n is a, c, g, or t
misc_difference         233
                        note = misc_feature - n is a, c, g, or t
misc_difference         234
                        note = misc_feature - n is a, c, g, or t
SEQUENCE: 15
caagcagaag acggcatacg agatcagatc gtgactggag ttcagacgtg tgctcttccg      60
atctnnnnnn nnnnnnnnnn nngtggccga tgtttcgcat cggcgtacga ctnnnnnnnn     120
atccacgtgc ttccccgcgc tgcatacttg nnnnnnnncc catgatcgtc cgaaggccag     180
agcattcgtt tttttttttt tttvnnnnnn nnnnnnnnnn nnnnnnnnnn nnnnagatcg     240
gaagagcgtc gtgtagggaa agagtgtaga tctcggtggt cgccgtatca tt             292
```

METHODS AND KITS FOR LABELING CELLULAR MOLECULES

CROSS-REFERENCES TO RELATED APPLICATIONS

This application is a Track 1 continuation of U.S. patent application Ser. No. 18/650,305, filed Apr. 30, 2024, which is a Track 1 continuation of U.S. patent application Ser. No. 18/536,654, filed Dec. 12, 2023, now U.S. Pat. No. 11,987, 838, issued on May 21, 2024, which is a Track 1 continuation of U.S. patent application Ser. No. 17/814,771, filed Jul. 25, 2022, which is a Track 1 continuation of U.S. patent application Ser. No. 17/695,671, filed Mar. 15, 2022, now U.S. Pat. No. 11,555,216, issued Jan. 17, 2023, which is a Track 1 continuation of U.S. application Ser. No. 17/521, 263, filed Nov. 8, 2021, now U.S. Pat. No. 11,427,856, issued Aug. 30, 2022, which is a Track 1 continuation of U.S. patent application Ser. No. 17/249,257, filed Feb. 25, 2021, now U.S. Pat. No. 11,168,355, issued Nov. 9, 2021, which is a Track 1 continuation of U.S. patent application Ser. No. 17/122,321, filed Dec. 15, 2020, now U.S. Pat. No. 11,634,751, issued Apr. 25, 2023, which is a continuation of U.S. patent application Ser. No. 14/941,433, filed Nov. 13, 2015, now U.S. Pat. No. 10,900,065, issued Jan. 26, 2021, which claims the benefit of U.S. Provisional Application No. 62/080,055, filed Nov. 14, 2014, each of which is hereby incorporated by reference in its entirety.

STATEMENT OF GOVERNMENT LICENSE RIGHTS

This invention was made with government support under Grant No. R01 CA207029, awarded by the National Institutes of Health, and Grant No. CCF-1317653, awarded by the National Science Foundation. The government has certain rights in the invention.

STATEMENT REGARDING SEQUENCE LISTING

The Sequence Listing XML associated with this application is provided in XML format and is hereby incorporated by reference into the specification. The name of the XML file containing the sequence listing is 3915-P1043US_CON23_UW_SL.xml. The XML file is 205 KB; was created on Jan. 23, 2023; and is being submitted electronically via Patent Center with the filing of the specification.

TECHNICAL FIELD

The present disclosure relates generally to methods of uniquely labeling or barcoding molecules within a cell, a plurality of cells, and/or a tissue. The present disclosure also relates to kits for uniquely labeling molecules within a cell, a plurality of cells, and/or a tissue. In particular, the methods and kits may relate to the labeling of RNAs, cDNAs, DNAs, proteins, peptides, and/or antigens.

BACKGROUND

Next Generation Sequencing (NGS) can be used to identify and/or quantify individual transcripts from a sample of cells. However, such techniques may be too complicated to perform on individual cells in large samples. In such methods, RNA transcripts are generally purified from lysed cells (i.e., cells that have been broken apart), followed by conversion of the RNA transcripts into complementary DNA (cDNA) using reverse transcription. The cDNA sequences can then be sequenced using NGS. In such a procedure, all of the cDNA sequences are mixed together before sequencing, such that RNA expression is measured for a whole sample and individual sequences cannot be linked back to an individual cell.

Methods for uniquely labeling or barcoding transcripts from individual cells can involve the manual separation of individual cells into separate reaction vessels and can require specialized equipment. An alternative approach to sequencing individual transcripts in cells is to use microscopy to identify individual fluorescent bases. However, this technique can be difficult to implement and limited to sequencing a low number of cells.

BRIEF DESCRIPTION OF THE DRAWINGS

The embodiments disclosed herein will become more fully apparent from the following description and appended claims, taken in conjunction with the accompanying drawings.

FIGS. 2A-2E is a schematic representation of the formation of cDNA by in situ reverse transcription. FIG. 2A depicts a cell that is fixed and permeabilized. FIG. 2B depicts addition of a poly(T) primer, which can template the reverse transcription of polyadenylated transcripts. FIG. 2C depicts addition of a random hexamer, which can template the reverse transcription of substantially any transcript. FIG. 2D depicts the addition of a primer that is designed to target a specific transcript such that only a subset of transcripts may be amplified. FIG. 2E depicts the cell of FIG. 2A after reverse transcription, illustrating a cDNA hybridized to an RNA.

FIG. 4 depicts primer binding.

FIG. 5 depicts primer binding followed by reverse transcription.

FIG. 17 also illustrates a region for a sample index, which is GATCTG in this embodiment.

DETAILED DESCRIPTION

Figure 1:
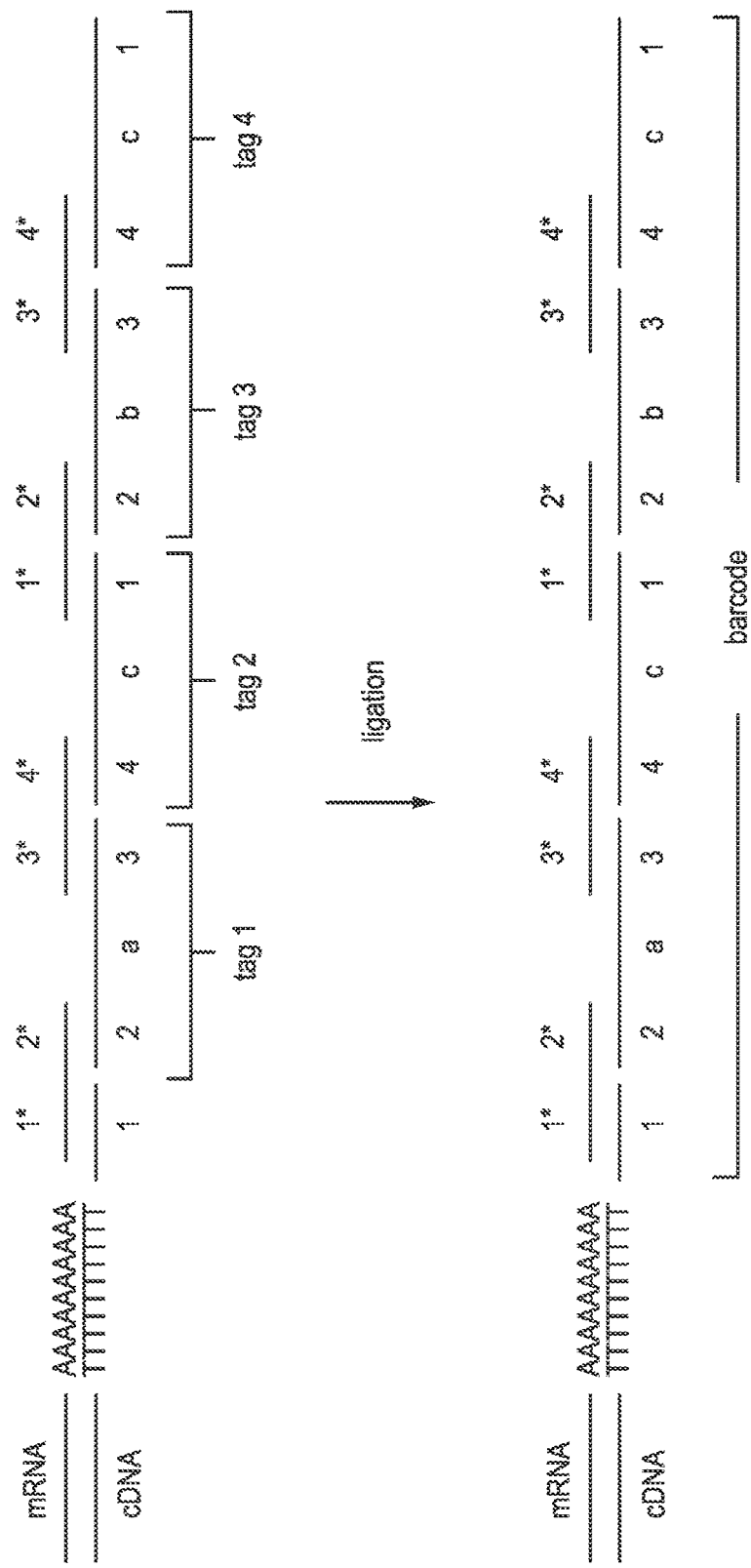
FIG. 1 depicts ligation of nucleic acid tags to form a label or barcode.

The present disclosure relates generally to methods of uniquely labeling or barcoding molecules within a cell, a plurality of cells, and/or a tissue. The present disclosure also relates to kits for uniquely labeling or barcoding molecules within a cell, a plurality of cells, and/or a tissue. The molecules to be labeled may include, but are not limited to, RNAs, cDNAs, DNAs, proteins, peptides, and/or antigens.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

The term "binding" is used broadly throughout this disclosure to refer to any form of attaching or coupling two or more components, entities, or objects. For example, two or more components may be bound to each other via chemical bonds, covalent bonds, ionic bonds, hydrogen bonds, electrostatic forces, Watson-Crick hybridization, etc.

A first aspect of the disclosure relates to methods of labeling nucleic acids. In some embodiments, the methods may comprise labeling nucleic acids in a first cell. The methods may comprise: (a) generating complementary DNAs (cDNAs) within a plurality of cells comprising the first cell by reverse transcribing RNAs using a reverse transcription primer comprising a 5' overhang sequence; (b) dividing the plurality of cells into a number (n) of aliquots; (c) providing a plurality of nucleic acid tags to each of the n aliquots, wherein each labeling sequence of the plurality of nucleic acid tags provided into a given aliquot is the same, and wherein a different labeling sequence is provided into each of the n aliquots; (d) binding at least one of the cDNAs in each of the n aliquots to the nucleic acid tags; (e) combining the n aliquots; and (f) repeating steps (b), (c), (d), and (e) with the combined aliquot. In various embodiments, the plurality of cells may be selected from eukaryotic cells and prokaryotic cells. In various other embodiments, the plurality of cells may be selected from, but not limited to, at least one of mammalian cells, yeast cells, and/or bacterial cells.

In certain embodiments, each nucleic acid tag may comprise a first strand including a 3' hybridization sequence extending from a 3' end of a labeling sequence and a 5' hybridization sequence extending from a 5' end of the labeling sequence. Each nucleic acid tag may also comprise a second strand including an overhang sequence. The overhang sequence may include (i) a first portion complementary to at least one of the 5' hybridization sequence and the 5' overhang sequence and (ii) a second portion complementary to the 3' hybridization sequence. In some embodiments, the nucleic acid tag (e.g., the final nucleic acid tag) may comprise a capture agent such as, but not limited to, a 5' biotin. A cDNA labeled with a 5' biotin-comprising nucleic acid tag may allow or permit the attachment or coupling of the cDNA to a streptavidin-coated magnetic bead. In some other embodiments, a plurality of beads may be coated with a capture strand (i.e., a nucleic acid sequence) that is configured to hybridize to a final sequence overhang of a barcode. In yet some other embodiments, cDNA may be purified or isolated by use of a commercially available kit (e.g., an RNEASY™ kit).

In various embodiments, step (f) (i.e., steps (b), (c), (d), and (e)) may be repeated a number of times sufficient to generate a unique series of labeling sequences for the cDNAs in the first cell. Stated another way, step (f) may be repeated a number of times such that the cDNAs in the first cell may have a first unique series of labeling sequences, the cDNAs in a second cell may have a second unique series of labeling sequences, the cDNAs in a third cell may have a third unique series of labeling sequences, and so on. The methods of the present disclosure may provide for the labeling of cDNA sequences from single cells with unique barcodes, wherein the unique barcodes may identify or aid in identifying the cell from which the cDNA originated. In other words, a portion, a majority, or substantially all of the cDNA from a single cell may have the same barcode, and that barcode may not be repeated in cDNA originating from one or more other cells in a sample (e.g., from a second cell, a third cell, a fourth cell, etc.).

In some embodiments, barcoded cDNA can be mixed together and sequenced (e.g., using NGS), such that data can be gathered regarding RNA expression at the level of a single cell. For example, certain embodiments of the methods of the present disclosure may be useful in assessing, analyzing, or studying the transcriptome (i.e., the different RNA species transcribed from the genome of a given cell) of one or more individual cells.

As discussed above, an aliquot or group of cells can be separated into different reaction vessels or containers and a first set of nucleic acid tags can be added to the plurality of cDNA transcripts. The aliquots of cells can then be regrouped, mixed, and separated again and a second set of nucleic acid tags can be added to the first set of nucleic acid tags. In various embodiments, the same nucleic acid tag may be added to more than one aliquot of cells in a single or given round of labeling. However, after repeated rounds of separating, tagging, and repooling, the cDNAs of each cell may be bound to a unique combination or sequence of nucleic acid tags that form a barcode. In some embodiments, cells in a single sample may be separated into a number of different reaction vessels. For example, the number of reaction vessels may include four 1.5 ml microcentrifuge tubes, a plurality of wells of a 96-well plate, or another suitable number and type of reaction vessels.

In certain embodiments, step (f) (i.e., steps (b), (c), (d), and (e)) may be repeated a number of times wherein the number of times is selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, etc. In certain other embodiments, step (f) may be repeated a sufficient number of times such that the cDNAs of each cell would be likely to be bound to a unique barcode. The number of times may be selected to provide a greater than 50% likelihood, greater than 90% likelihood, greater than 95% likelihood, greater than 99% likelihood, or some other probability that the cDNAs in each cell are bound to a unique barcode. In yet other embodiments, step (f) may be repeated some other suitable number of times.

In some embodiments, the methods of labeling nucleic acids in the first cell may comprise fixing the plurality of cells prior to step (a). For example, components of a cell may be fixed or cross-linked such that the components are immobilized or held in place. The plurality of cells may be fixed using formaldehyde in phosphate buffered saline (PBS). The plurality of cells may be fixed, for example, in about 4% formaldehyde in PBS. In various embodiments, the plurality of cells may be fixed using methanol (e.g., 100% methanol) at about −20° C. or at about 25° C. In various other embodiments, the plurality of cells may be fixed using methanol (e.g., 100% methanol), at between about −20° C. and about 25° C. In yet various other embodiments, the plurality of cells may be fixed using ethanol (e.g., about 70-100% ethanol) at about −20° C. or at room temperature. In yet various other embodiments, the plurality of cells may be fixed using ethanol (e.g., about 70-100% ethanol) at between about −20° C. and room temperature. In still various other embodiments, the plurality of cells may be fixed using acetic acid, for example, at about −20° C. In still various other embodiments, the plurality of cells may be fixed using acetone, for example, at about −20° C. Other suitable methods of fixing the plurality of cells are also within the scope of this disclosure.

In certain embodiments, the methods of labeling nucleic acids in the first cell may comprise permeabilizing the plurality of cells prior to step (a). For example, holes or openings may be formed in outer membranes of the plurality of cells. TRITON™ X-100 may be added to the plurality of cells, followed by the addition of HCl to form the one or more holes. About 0.2% TRITON™ X-100 may be added to the plurality of cells, for example, followed by the addition of about 0.1 N HCl. In certain other embodiments, the plurality of cells may be permeabilized using ethanol (e.g., about 70% ethanol), methanol (e.g., about 100% methanol), Tween 20 (e.g., about 0.2% Tween 20), and/or NP-40 (e.g., about 0.1% NP-40). In various embodiments, the methods of labeling nucleic acids in the first cell may comprise fixing and permeabilizing the plurality of cells prior to step (a).

In some embodiments, the cells may be adherent cells (e.g., adherent mammalian cells). Fixing, permeabilizing, and/or reverse transcription may be conducted or performed on adherent cells (e.g., on cells that are adhered to a plate). For example, adherent cells may be fixed, permeabilized, and/or undergo reverse transcription followed by trypsinization to detach the cells from a surface. Alternatively, the adherent cells may be detached prior to the separation and/or tagging steps. In some other embodiments, the adherent cells may be trypsinized prior to the fixing and/or permeabilizing steps.

In some embodiments, the methods of labeling nucleic acids in the first cell may comprise ligating at least two of the nucleic acid tags that are bound to the cDNAs. Ligation may be conducted before or after the lysing and/or the cDNA purification steps. Ligation can comprise covalently linking the 5' phosphate sequences on the nucleic acid tags to the 3' end of an adjacent strand or nucleic acid tag such that individual tags are formed into a continuous, or substantially continuous, barcode sequence that is bound to the 3' end of the cDNA sequence. In various embodiments, a double-stranded DNA or RNA ligase may be used with an additional linker strand that is configured to hold a nucleic acid tag together with an adjacent nucleic acid in a "nicked" double-stranded conformation. The double-stranded DNA or RNA ligase can then be used to seal the "nick." In various other embodiments, a single-stranded DNA or RNA ligase may be used without an additional linker. In certain embodiments, the ligation may be performed within the plurality of cells.

FIG. 1 illustrates ligation of a plurality of nucleic acid tags to form a substantially continuous label or barcode. For example, after a plurality of nucleic acid tag additions, each cDNA transcript may be bound or linked to series of nucleic acid tags. Use of a ligase may ligate or covalently link a portion of the nucleic acid tags to form a substantially continuous label or barcode that is bound or attached to a cDNA transcript.

In certain other embodiments, the methods may comprise lysing the plurality of cells (i.e., breaking down the cell structure) to release the cDNAs from within the plurality of cells, for example, after step (f). In some embodiments, the plurality of cells may be lysed in a lysis solution (e.g., 10 mM Tris-HCl (pH 7.9), 50 mM EDTA (pH 7.9), 0.2 M NaCl, 2.2% SDS, 0.5 mg/ml ANTI-RNase (a protein ribonuclease inhibitor; AMBION®) and 1000 mg/ml proteinase K (AMBION®)), for example, at about 55° C. for about 3 hours with shaking (e.g., vigorous shaking). In some other embodiments, the plurality of cells may be lysed using ultrasonication and/or by being passed through an 18-25 gauge syringe needle at least once. In yet some other embodiments, the plurality of cells may be lysed by being heated to about 70-90° C. For example, the plurality of cells may be lysed by being heated to about 70-90° C. for about one or more hours. The cDNAs may then be isolated from the lysed cells. In some embodiments, RNase H may be added to the cDNA to remove RNA. The methods may further comprise ligating at least two of the nucleic acid tags that are bound to the released cDNAs. In some other embodiments, the methods of labeling nucleic acids in the first cell may comprise ligating at least 3, 4, 5, 6, 7, 8, 9, 10, 11, 12, 13, 14, 15, 16, 17, 18, 19, 20, 21, 22, 23, 24, 25, 30, 35, 40, 45, 50, etc. of the nucleic acid tags that are bound to the cDNAs.

In various embodiments, the methods of labeling nucleic acids in the first cell may comprise removing one or more unbound nucleic acid tags (e.g., washing the plurality of cells). For example, the methods may comprise removing a portion, a majority, or substantially all of the unbound nucleic acid tags. Unbound nucleic acid tags may be removed such that further rounds of the disclosed methods are not contaminated with one or more unbound nucleic acid tags from a previous round of a given method. In some embodiments, unbound nucleic acid tags may be removed via centrifugation. For example, the plurality of cells can be centrifuged such that a pellet of cells is formed at the bottom of a centrifuge tube. The supernatant (i.e., liquid containing the unbound nucleic acid tags) can be removed from the centrifuged cells. The cells may then be resuspended in a buffer (e.g., a fresh buffer that is free or substantially free of unbound nucleic acid tags). In another example, the plurality of cells may be coupled or linked to magnetic beads that are coated with an antibody that is configured to bind the cell membrane. The plurality of cells can then be pelleted using a magnet to draw them to one side of the reaction vessel. In some other embodiments, the plurality of cells may be placed in a cell strainer (e.g., a PLURISTRAINER® cell strainer) and washed with a wash buffer. For example, the plurality of cells may remain in the cell strainer while the wash buffer passes through the cell strainer. Wash buffer may include a surfactant, a detergent, and/or about 5-60% formamide.

As discussed above, the plurality of cells can be repooled and the method can be repeated any number of times, adding more tags to the cDNAs creating a set of nucleic acid tags that can act as a barcode. As more and more rounds are added, the number of paths that a cell can take increases and consequently the number of possible barcodes that can be created also increases. Given enough rounds and divisions, the number of possible barcodes will be much higher than the number of cells, resulting in each cell likely having a unique barcode. For example, if the division took place in a 96-well plate, after 4 divisions there would be $96^4$-84,934,656 possible barcodes.

In some embodiments, the reverse transcription primer may be configured to reverse transcribe all, or substantially all, RNA in a cell (e.g., a random hexamer with a 5' overhang). In some other embodiments, the reverse transcription primer may be configured to reverse transcribe RNA having a poly(A) tail (e.g., a poly(dT) primer, such as a dT(15) primer, with a 5' overhang). In yet some other embodiments, the reverse transcription primer may be configured to reverse transcribe predetermined RNAs (e.g., a transcript-specific primer). For example, the reverse transcription primer may be configured to barcode specific transcripts such that fewer transcripts may be profiled per cell, but such that each of the transcripts may be profiled over a greater number of cells.

FIGS. 2A-2E illustrate the formation of cDNA by in situ reverse transcription. FIG. 2A depicts a cell that is fixed and permeabilized. FIG. 2B depicts addition of a poly(T) primer, as discussed above, which can template the reverse transcription of polyadenylated transcripts. FIG. 2C depicts addition of a random hexamer, as discussed above, which can template the reverse transcription of substantially any transcript. FIG. 2D depicts the addition of a primer that is designed to target a specific transcript, as discussed above, such that only a subset of transcripts may be amplified. FIG. 2E depicts the cell of FIG. 2A after reverse transcription, illustrating a cDNA hybridized to an RNA.

Reverse transcription may be conducted or performed on the plurality of cells. In certain embodiments, reverse transcription may be conducted on a fixed and/or permeabilized plurality of cells. In some embodiments, M-MuLV reverse transcriptase (ENZYMATICS™) may be used in the reverse transcription. Any suitable method of reverse transcription is within the scope of this disclosure. For example, a reverse transcription mix may include a reverse transcription primer including a 5' overhang and the reverse transcription primer may be configured to initiate reverse transcription and/or to act as a binding sequence for nucleic acid tags. In some other embodiments, a portion of a reverse transcription primer that is configured to bind to RNA and/or initiate reverse transcription may comprise one or more of the following: a random hexamer, a septamer, an octomer, a nonamer, a decamer, a poly(T) stretch of nucleotides, and/or one or more gene specific primers.

Another aspect of the disclosure relates to methods of uniquely labeling molecules within a cell or within a plurality of cells. In some embodiments, the method may comprise: (a) binding an adapter sequence, or universal adapter, to molecules within the plurality of cells; (b) dividing the plurality of cells into at least two primary aliquots, wherein the at least two primary aliquots comprise at least a first primary aliquot and a second primary aliquot; (c) providing primary nucleic acid tags to the at least two primary aliquots, wherein the primary nucleic acid tags provided to the first primary aliquot are different from the primary nucleic acid tags provided to the second primary aliquot; (d) binding the adapter sequences within each of the at least two primary aliquots with the provided primary nucleic acid tags; (e) combining the at least two primary aliquots; (f) dividing the combined primary aliquots into at least two secondary aliquots, the at least two secondary aliquots comprising at least a first secondary aliquot and a second secondary aliquot; (g) providing secondary nucleic acid tags to the at least two secondary aliquots, wherein the secondary nucleic acid tags provided to the first secondary aliquot are different from the secondary nucleic acid tags provided to the second secondary aliquot; and (h) binding the molecules within each of the at least two secondary aliquots with the provided secondary nucleic acid tags.

In certain embodiments, the method may further comprise step (i), i.e., repeating steps (c), (f), (g), and (h) with subsequent aliquots. Step (i) can be repeated a number of times sufficient to generate a unique series of nucleic acid tags for the molecules in a single cell. In various embodiments, the number of times may be selected from 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, etc. In certain other embodiments, step (i) may be repeated another suitable number of times.

In some embodiments, the molecules may be disposed within the cell or within the plurality of cells. In some other embodiments, the molecules may be coupled to the cell or to the plurality of cells. For example, the molecules may be cell-surface molecules. In yet some other embodiments, the molecules may be disposed within and/or coupled to the cell or the plurality of cells.

As discussed above, the method may comprise fixing and/or permeabilizing the plurality of cells prior to step (a). In various embodiments, each of the nucleic acid tags may comprise a first strand. The first strand may comprise a barcode sequence including a 3' end and a 5' end. The first strand may further comprise a 3' hybridization sequence and a 5' hybridization sequence flanking the 3' end and the 5' end of the barcode sequence, respectively. In some embodiments, each of the nucleic acid tags may comprise a second strand. The second strand may comprise a first portion complementary to at least one of the 5' hybridization sequence and the adapter sequence and a second portion complementary to the 3' hybridization sequence.

In certain embodiments, the molecules are macromolecules. In various embodiments, the molecules are selected from at least one of RNA, cDNA, DNA, protein, peptides, and/or antigens.

In some embodiments, the molecules are RNA and the adapter sequence may be single-stranded. Furthermore, step (a) may comprise one of ligating a 5' end of the single-stranded adapter sequence to a 3' end of the RNA and/or ligating a 3' end of the single-stranded adapter sequence to a 5' end of the RNA. In some other embodiments, the molecules are RNA and step (a) may comprise hybridizing the adapter sequence to the RNA.

Figure 3A:
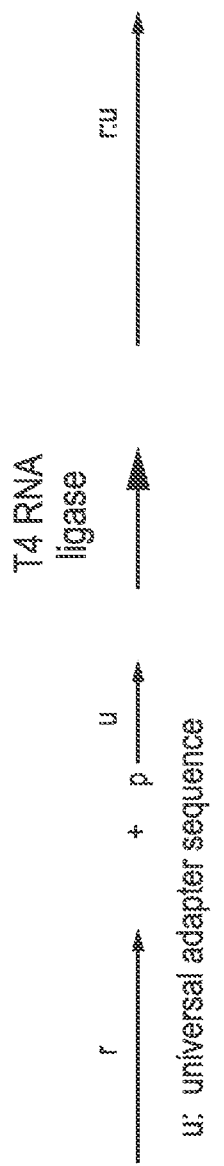
FIG. 3A depicts non-templated ligation of a single-stranded adapter to an RNA fragment.
Figure 3B:
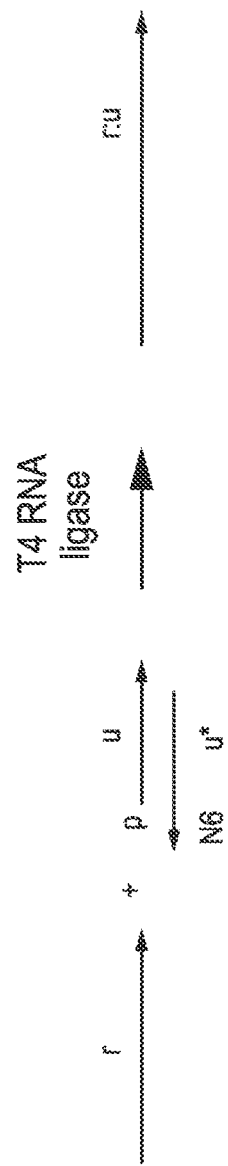
FIG. 3B depicts ligation of a single-stranded adapter using a partial duplex with random hexamer primers.

Methods related to binding or coupling an adapter sequence to an RNA can be used, for example, in RNA transcriptome sequencing, ribosome profiling, small RNA sequencing, non-coding coding RNA sequencing, and/or RNA structure profiling. In some embodiments, the plurality of cells may be fixed and/or permeabilized. The 5' end of a single-stranded adapter sequence may be ligated to the 3' end of an RNA (see FIGS. 3A and 3B). In certain embodiments, the ligation may be conducted or performed by T4 RNA Ligase 1. In certain other embodiments, the ligation may be conducted by T4 RNA Ligase 1 with a single-stranded adapter sequence including a 5' phosphate. In various embodiments, the ligation may be conducted by THERMOSTABLE 5' APPDNA/RNA LIGASE™ (NEW ENGLAND BIOLABS®). In various other embodiments, the ligation may be conducted by THERMOSTABLE 5' APPDNA/RNA LIGASE™ with a 5' pre-adenylated single-stranded adapter sequence. Other suitable ligases and adapter sequences are also within the scope of this disclosure.

In some embodiments, the RNA can be labeled with adapter sequence using hybridization, for example, via Watson-Crick base-pairing (see FIG. 4). After the labeling steps and/or cell lysis, as discussed above, the adapter sequence may be configured to prime reverse transcription to form or generate cDNA (see FIG. 5).

The 3' end of a single-stranded adapter sequence may be ligated to the 5' end of an RNA. In certain embodiments, the ligation may be conducted or performed by T4 RNA Ligase 1. In certain other embodiments, the ligation may be conducted by T4 RNA Ligase 1 with an RNA including a 5' phosphate. In various embodiments, the ligation may be conducted by THERMOSTABLE 5' APPDNA/RNA LIGASE™ (NEW ENGLAND BIOLABS®). In various other embodiments, the ligation may be conducted by THERMOSTABLE 5' APPDNA/RNA LIGASE™ with a 5' pre-adenylated RNA. As stated above, other suitable ligases and adapter sequences are also within the scope of this disclosure.

In some embodiments, the molecules may be cDNA. Methods related to binding or coupling an adapter sequence to a cDNA can be used, for example, in RNA transcriptome sequencing. In certain embodiments, the plurality of cells may be fixed and/or permeabilized. Reverse transcription may be performed on the plurality of fixed and/or permeabilized cells with a primer that includes the adapter sequence on the 5' end. As discussed above, the 3' end of the primer may be gene-specific, a random hexamer, or a poly(T) sequence. The resulting cDNA may include the adapter sequence on its 5' end (see FIG. 5).

In some embodiments, wherein the molecules are DNA (e.g., genomic DNA), the method may further comprise digesting the DNA with a restriction enzyme prior to step (a). Furthermore, step (a) may comprise ligating the adapter sequence to the digested DNA.

Methods related to binding or coupling an adapter sequence to a DNA may be used, for example, in whole genome sequencing, targeted genome sequencing, DNase-Seq, ChIP-sequencing, and/or ATAC-seq. In certain embodiments, one or more restriction enzymes may be used to digest DNA into at least one of blunt end fragments and/or fragments having overhang sequences. A partial double-stranded sequence with the single-stranded universal adapter or adapter sequence protruding on one end can be ligated to the digested genomic DNA. For example, a partial double-stranded sequence with the single-stranded adapter sequence having an overhang, wherein the overhang is compatible with the overhang generated by the one or more restriction enzymes, may be ligated to the digested genomic DNA.

In various embodiments, adapter sequences can be integrated (e.g., directly integrated) into genomic DNA using Tn5 transposase and the transposase can be released to expose the adapter sequences by addition of sodium dodecyl sulfate (SDS). Other transposases and methods of integrating the adapter sequences into genomic DNA are also within the scope of this disclosure.

In certain embodiments, the molecules are protein, peptide, and/or antigen, and the adapter sequence may be bound to a unique identifier sequence (e.g., comprising nucleic acids) that is coupled to an antibody. The unique identifier sequence may be configured to uniquely identify the antibody to which the unique identifier sequence is bound. Furthermore, step (a) may comprise binding the antibodies, which comprise each of the adapter sequence and the unique identifier sequence, to the protein, peptide, and/or antigen. In certain other embodiments, the molecules are protein, peptide, and/or antigen, and the adapter sequence may be integrated in an aptamer. Furthermore, step (a) may comprise binding the aptamer to the protein, peptide, and/or antigen.

Figure 6:
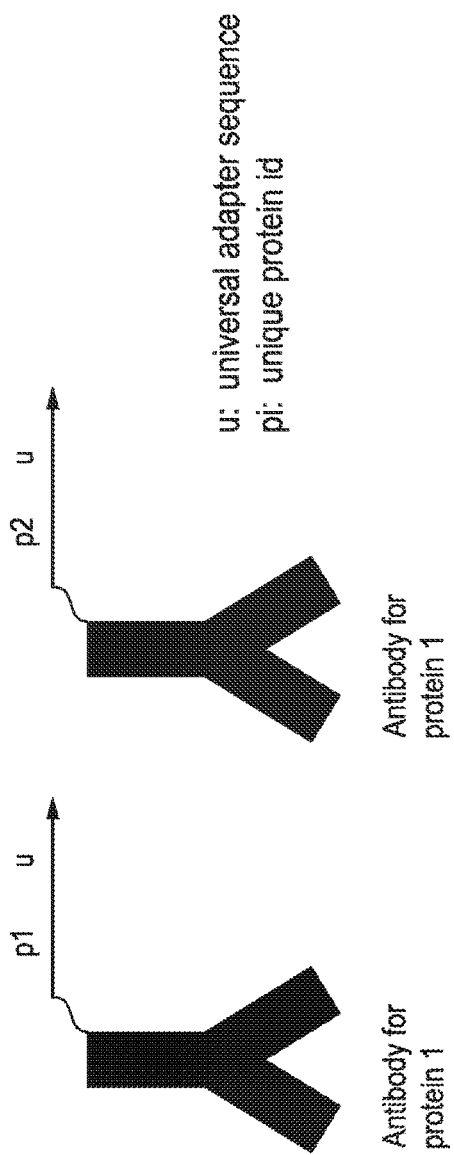
FIG. 6 depicts DNA-tagged antibodies for use in labeling cellular proteins.

Methods related to binding or coupling an adapter sequence to a protein, a peptide, and/or an antigen may be used, for example, in protein quantification, peptide quantification, and/or antigen quantification. In various embodiments, the adapter sequence can be attached (e.g., chemically attached) to an antibody. For example, the adapter sequence can be attached to an antibody using chemistry known to the skilled artisan for mediating DNA-protein bonds. Antibodies for different proteins can be labeled with nucleic acid sequences or strands that include a unique identifier sequence in addition to the adapter sequence. The antibody, or set of antibodies, may then be used in an immunostaining experiment to label a protein, or set of proteins, in fixed and/or permeabilized cells or tissue (see FIG. 6). Subsequently, the cells may undergo a labeling or barcoding procedure as disclosed herein.

In some embodiments, the nucleic acid sequences (e.g., the DNA molecules) attached or bound to the antibodies can be released from the antibodies and/or adapter sequences. A sequencing reaction can reveal a unique identifier sequence associated with a given protein as well as the label or barcode associated with a unique cell or cells. In certain embodiments, such a method may reveal or identify the number and/or type of proteins present in one or more cells.

Figure 7:
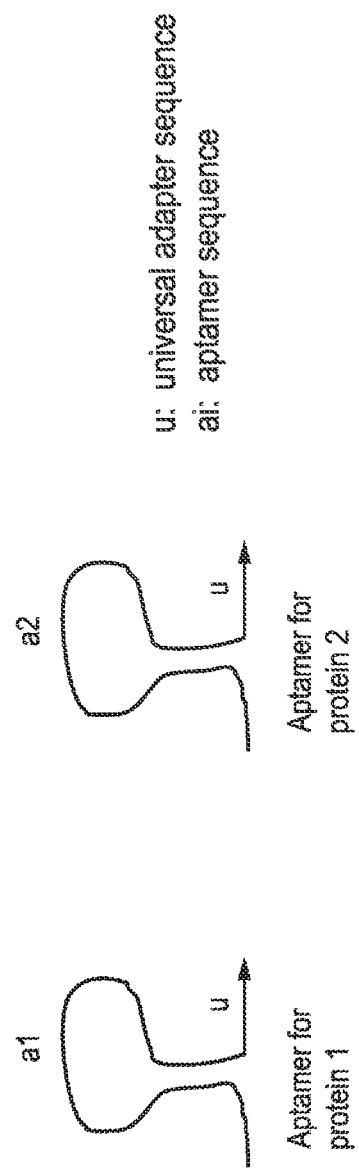
FIG. 7 depicts aptamers for use in labeling cellular proteins.

In various embodiments, a DNA aptamer and/or an RNA aptamer can be used instead of, or in addition to, a nucleic acid-modified (or DNA-modified) antibody as described above (see FIG. 7). The adapter sequence (and target protein-specific antibody) may be integrated (e.g., directly integrated) into the sequence of a given aptamer.

Another aspect of the disclosure relates to methods of barcoding nucleic acids within a cell. In some embodiments, the methods of barcoding nucleic acids within a cell may comprise: (a) generating cDNAs within a plurality of cells by reverse transcribing RNAs using a reverse transcription primer comprising a 5' overhang sequence; (b) dividing the plurality of cells into at least two aliquots; (c) providing a plurality of nucleic acid tags to each of the at least two aliquots, wherein each barcode sequence of the plurality of nucleic acid tags introduced into a given aliquot is the same, and wherein a different barcode sequence is introduced into each aliquot; (d) binding at least one of the cDNAs in each of the at least two aliquots to the nucleic acid tags; (e) combining the at least two aliquots; and (f) repeating steps (b), (c), (d), and (e) at least once with the combined aliquot.

In certain embodiments, each nucleic acid tag may comprise a first strand comprising a 3' hybridization sequence extending from a 3' end of a barcode sequence and a 5' hybridization sequence extending from a 5' end of the barcode sequence. Each nucleic acid tag may also comprise a second strand comprising an overhang sequence, wherein the overhang sequence comprises (i) a first portion complementary to at least one of the 5' hybridization sequence and the 5' overhang sequence and (ii) a second portion complementary to the 3' hybridization sequence.

Figure 8:
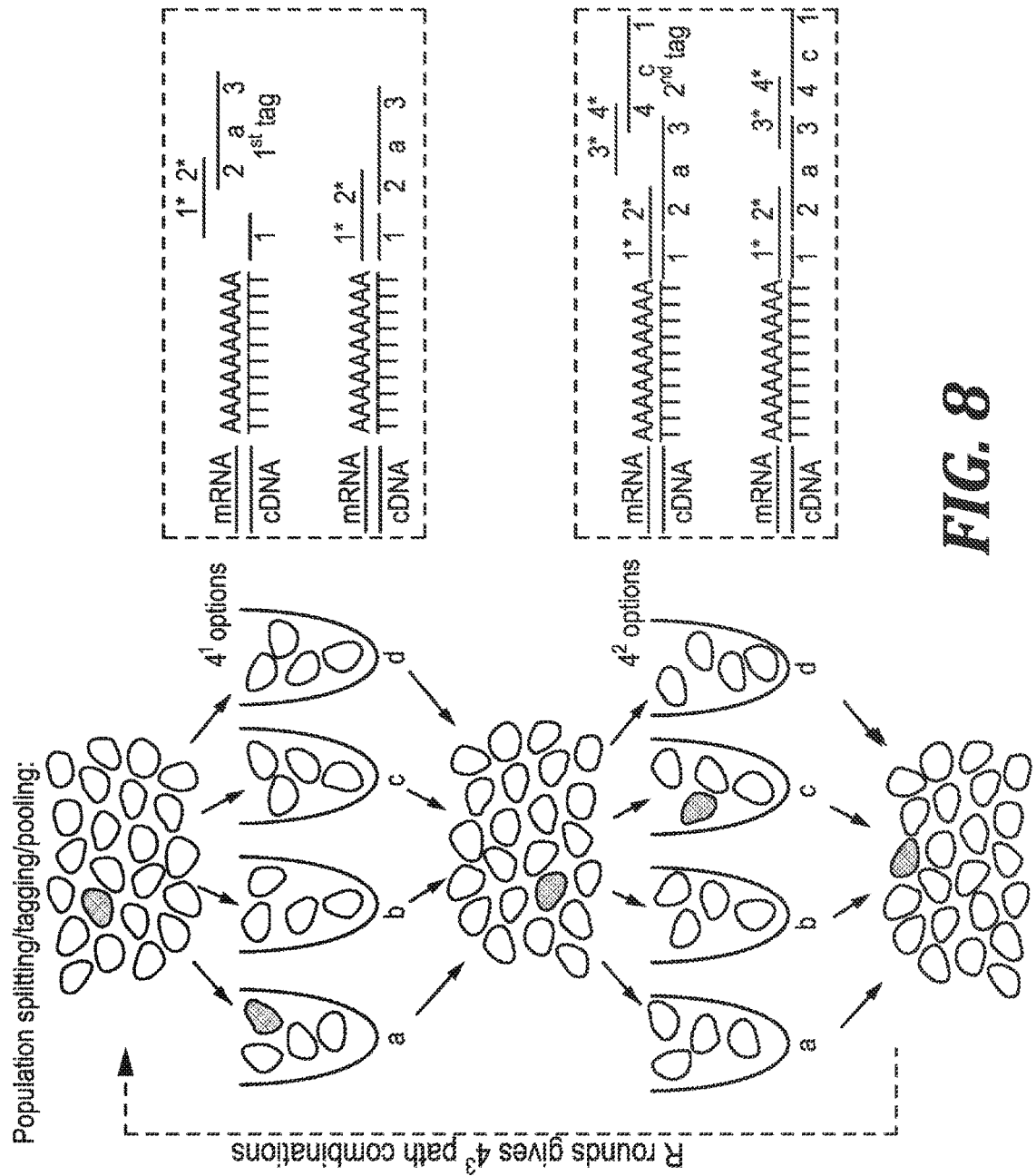
FIG. 8 is a schematic representation of the dividing, tagging, and pooling of cells, according to an embodiment of the present disclosure. As depicted, cells can be divided between a plurality of reaction vessels. One cell is highlighted to show its path through the illustrated process.
Figures 9A, 9B, 10:
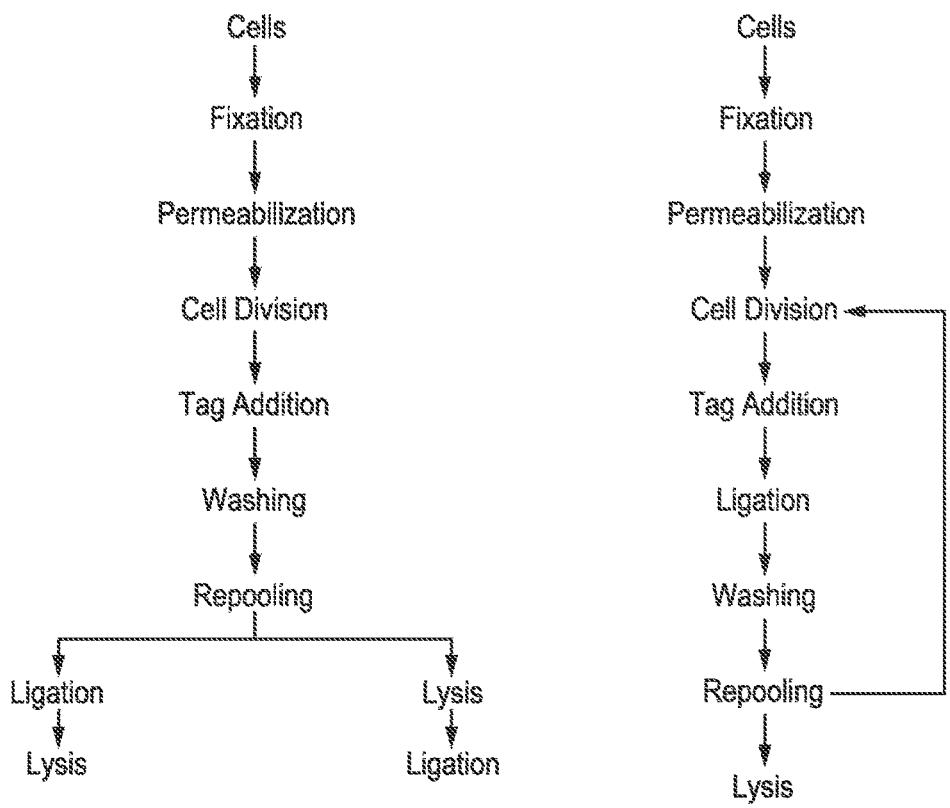
FIG. 9A depicts an exemplary workflow, according to an embodiment of the present disclosure.
FIG. 9B depicts an exemplary workflow, according to another embodiment of the present disclosure.
FIG. 10 depicts a reverse transcription primer (BC_0055), according to an embodiment of the present disclosure.

FIG. 8 depicts dividing, tagging, and pooling of cells, according to an embodiment of the present disclosure. Cells that have been reverse transcribed can be divided between reaction vessels or wells. In FIG. 8, 4 wells are shown. As discussed above, however, any suitable number of reaction vessels or wells may be used. One cell is highlighted to show its path through the process. As depicted, the highlighted cell first ends up in well 'a', wherein it is the $1^{st}$ tag added to it that hybridizes to the overhang of all the cDNA transcripts (shown in the box). The tag carries a unique barcode region 'a', identifying the well that the cell was in. After hybridization, all cells are washed to remove excess tags, regrouped, and then split again between the same number of wells. The highlighted cell then ends up in well 'c' and has a $2^{nd}$ tag added to it identifying the well it was in. After the second round, the cells could have taken $4^2=16$ possible paths through the tubes. The process can be repeated, adding more tags to the cDNA transcripts and increasing the number of possible paths the cells can take. FIGS. 9A and 9B depict two exemplary workflows, according to embodiments of the present disclosure.

Another aspect of the disclosure relates to kits for labeling nucleic acids within at least a first cell. In some embodiments, the kit may comprise at least one reverse transcription primer comprising a 5' overhang sequence. The kit may also comprise a plurality of first nucleic acid tags. Each first nucleic acid tag may comprise a first strand. The first strand may include a 3' hybridization sequence extending from a 3' end of a first labeling sequence and a 5' hybridization sequence extending from a 5' end of the first labeling sequence. Each first nucleic acid tag may further comprise a second strand. The second strand may include an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence.

The kit may further comprise a plurality of second nucleic acid tags. Each second nucleic acid tag may comprise a first strand. The first strand may include a 3' hybridization sequence extending from a 3' end of a second labeling sequence and a 5' hybridization sequence extending from a 5' end of the second labeling sequence. Each second nucleic acid tag may further comprise a second strand. The second strand may comprise an overhang sequence, wherein the overhang sequence may comprise (i) a first portion complementary to at least one of the 5' hybridization sequence and the 5' overhang sequence of the reverse transcription primer and (ii) a second portion complementary to the 3' hybridization sequence. In some embodiments, the first labeling sequence may be different from the second labeling sequence.

In some embodiments, the kit may also comprise one or more additional pluralities of nucleic acid tags. Each nucleic acid tag of the one or more additional pluralities of nucleic acid tags may comprise a first strand. The first strand may include a 3' hybridization sequence extending from a 3' end of a labeling sequence and a 5' hybridization sequence extending from a 5' end of the labeling sequence. Each nucleic acid tag of the one or more additional pluralities of nucleic acid tags may also comprise a second strand. The second strand may include an overhang sequence, wherein the overhang sequence comprises (i) a first portion complementary to at least one of the 5' hybridization sequence and the 5' overhang sequence of the reverse transcription primer and (ii) a second portion complementary to the 3' hybridization sequence. In some embodiments, the labeling sequence may be different in each given additional plurality of nucleic acid tags.

In various embodiments, the kit may further comprise at least one of a reverse transcriptase, a fixation agent, a permeabilization agent, a ligation agent, and/or a lysis agent.

Another aspect of the disclosure relates to kits for labeling molecules within at least a first cell. For example, the kits as disclosed above may be adapted to label one or more of RNA, cDNA, DNA, protein, peptides, or antigens within at least a first cell.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Fixation and Reverse Transcription

NIH/3T3 (mouse) and Hela-S3 (human) cells can be grown to confluence on two separate 10 cm cell culture plates. The cells can be rinsed twice with 10 ml 1× phosphate buffered saline (PBS), 1 ml of 0.05% trypsin can be added to each plate, and the plates can be incubated at 37° C. for 5 minutes. The cells can be detached by tilting each plate at a 45° angle while pipetting trypsin across the plates, which can be continued until all, or substantially all, of the cells are detached. Each cell line can be transferred into its own 15 ml conical centrifuge tube (FALCON™). 2 ml of Dulbecco's Modified Eagle Medium (DMEM) with 10% fetal bovine serum (FBS) can be added to each tube. The number of cells in each tube can be calculated (e.g., with a hemocytometer or on a flow cytometer). For example, 200 µl of the sample can be transferred from each tube into separate 1.7 ml microcentrifuge tubes (EPPENDORF®) and 100 µl of the sample can be run on an ACCURI™ Flow Cytometer to calculate the cell concentration.

The same number of cells from each tube can be combined into a new single 15 ml conical centrifuge tube (FALCON™), using as many cells as possible. A 5 minute spin can be conducted at 500×g in a 15 ml conical centrifuge tube (FALCON™). It may be helpful to use a bucket centrifuge so that the cells are pelleted at the bottom of the tube rather than on the side of the tube. The liquid can be aspirated without disturbing the cell pellet and the cells can be resuspended in 500 µl of 4% formaldehyde. The cells can then be left at room temperature (i.e., 20-25° C.) for 10 minutes. 1.5 ml of 0.5% TRITON™ X-100 can be added to the tube and mixed gently with a pipette. The tube can them be spun at 500×g for 5 minutes. Again, the liquid can be aspirated without disturbing the pellet and the pellet can be washed twice with 1 ml PBS without resuspending the pellet. If washing disturbs the pellet, the second wash can be skipped. The pellet can then be resuspended in 1 ml 0.1N HCl and incubated at room temperature for 5 minutes.

2 ml of Tris-HCl (pH 8.0) can be added to a new 15 ml conical centrifuge tube (FALCON™). The fixed cells in HCl, from above, can be transferred to the tube with Tris-HCl so as to neutralize the HCl. The number of cells in the tube can then be calculated as discussed above (e.g., with a hemocytometer or on a flow cytometer). The fixed cells in Tris-HCl can be spun down at 500×g for 5 minutes and the liquid can be aspirated without disturbing the pellet. The pellet can be washed twice with 1 ml RNase-free molecular grade water, without disturbing the pellet. The cells can then be resuspended to a concentration of 2.5 million cells/ml (to do this, the concentration calculated before the last spin step can be used).

A reverse transcription mix can be made (55 µl M-MuLV reverse transcriptase buffer (ENZYMATICS™), 55 µl M-MuLV reverse transcriptase (ENZYMATICS™), 5.5 µl dNTPs (25 mM per base), 3.44 µl RNase inhibitor (ENZYMATICS™, 40 units/µl), 210.4 µl nuclease-free water, and 2.75 µl RT Primer (BC_0055, 100 µM)). In a well of a 24-well cell culture plate, 300 µl of the reverse transcription mix can be combined with 200 µl of the fixed cells (~500,000 cells) and mixed gently by pipetting. The mixture can then be incubated at room temperature for 10 minutes to allow the reverse transcription primer to anneal and the mixture can then be incubated at 37° C. in a humidified incubator overnight (i.e., ~16 hours).

A primer that can be used for reverse transcription (BC_0055) is depicted in FIG. 10. This is an anchored primer, designed to bind the start of a poly(A) tail of a messenger RNA. The primer may be synthesized with all 4 bases at the 3' end (N) and every base except T at the second-most 3' position (V). The primer can also include 15 consecutive dTs. In some embodiments, the primer may include more than 15 dTs. In some other embodiments, the primer may include fewer than 15 dTs. In embodiments wherein the primer includes fewer than 15 dTs, the melting temperature of the primer may be lowered. The domain s0 may not hybridize to messenger RNAs, but may instead provide an accessible binding domain for a linker oligo. The primer also includes a 5' phosphate that can allow ligation of the primer to another oligo by T4 DNA ligase.

Example 2—Preparation of Barcodes

The barcodes were ordered in 96-well plates at 100 µM concentrations. Each barcode was annealed with its corresponding linker oligo (see FIGS. 10-12).

Figure 11:
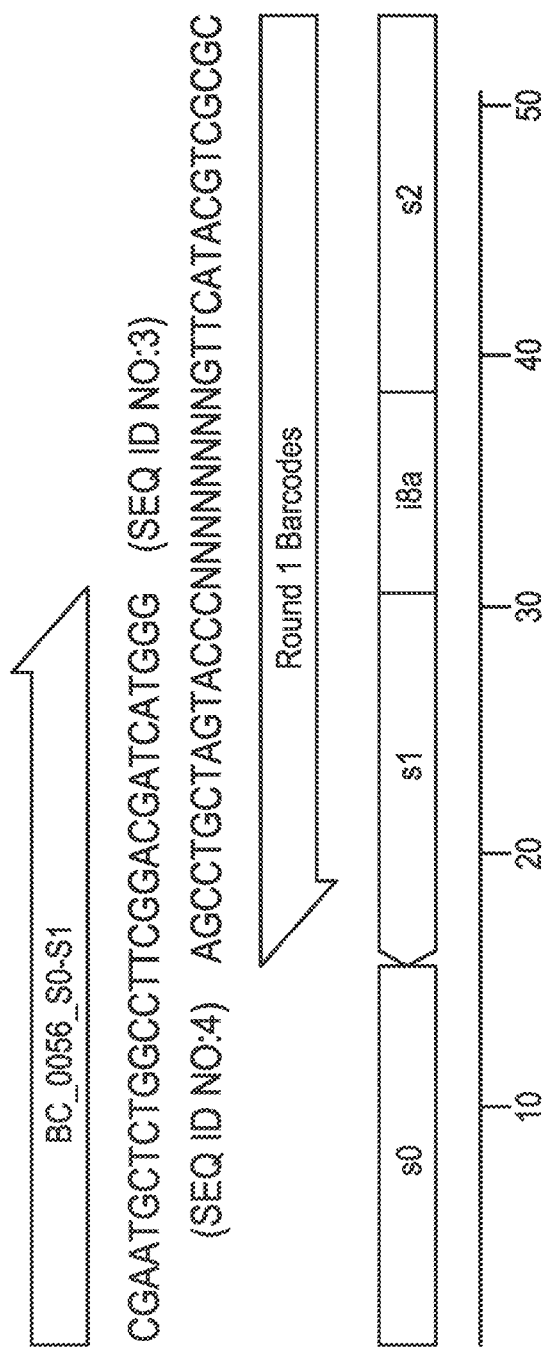
FIG. 11 depicts an annealed, first-round barcode oligo, according to an embodiment of the present disclosure.

FIG. 11 depicts an annealed, first-round barcode oligo. 96 first-round barcode oligos with unique sequences in domain i8a were used. In the first round, the unique sequence in domain i8a is the region of the sequence that is used as a barcode. By varying 8 nucleotides, there are 65,536 possible unique sequences. In some embodiments, more than 8 nucleotides may be present in domain i8a. In some other embodiments, fewer than 8 nucleotides may be present in domain i8a. The first-round barcodes were preannealed to a linker strand (BC_0056) through complementary sequences in domain s1. The linker strand can include complementary sequence to part of the reverse transcription primer (domain s0) that can allow it to hybridize and bring the 3' end of the first-round barcodes in close proximity to the 5' end of the reverse transcription primer. The phosphate of the reverse transcription primer can then be ligated to the 3' end of the first-round barcodes by T4 DNA ligase. The domain s2 can provide an accessible binding domain for a linker oligo to be used in another round of barcoding. The first-round barcode oligos can include a 5' phosphate that can allow ligation to the 3' end of another oligo by T4 DNA ligase.

Figure 12:
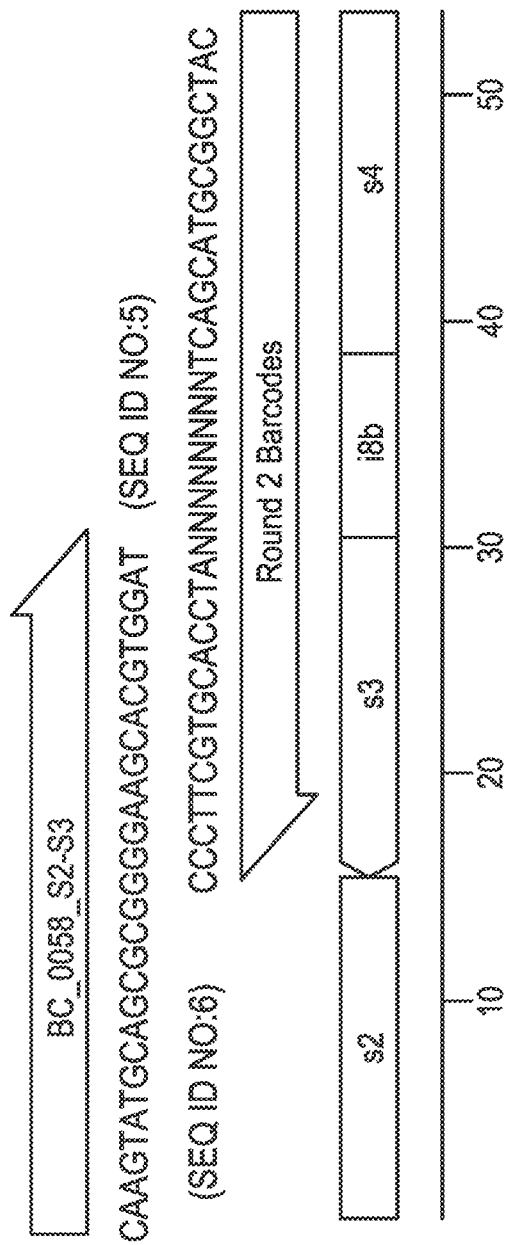
FIG. 12 depicts an annealed, second-round barcode oligo, according to an embodiment of the present disclosure.

FIG. 12 depicts an annealed, second-round barcode oligo. 96 second-round barcode oligos with unique sequences in domain i8b were used. In the second round, the unique sequence in domain i8b is the region of the sequence that is used as a barcode. By varying 8 nucleotides, there are 65,536 possible unique sequences. In some embodiments, more than 8 nucleotides may be present in domain i8b. In some embodiments, less than 8 nucleotides may be present in domain i8b. The second-round barcodes can be preannealed to a linker strand (BC_0058) through complementary sequences in domain s3. The linker strand can include complementary sequence to part of the first-round barcode oligo (domain s2) that can allow it to hybridize and bring the 3' end of the first-round barcodes in close proximity to the 5' end of the second-round barcode oligo. The phosphate of the first-round barcode oligo can then be ligated to the 3' end of the second-round barcodes by T4 DNA ligase. The domain s4 can provide an accessible binding domain for a linker oligo to be used in another round of barcoding. The second-round barcode oligos can include a 5' phosphate that can allow ligation to the 3' end of another oligo by T4 DNA ligase.

Figure 13:
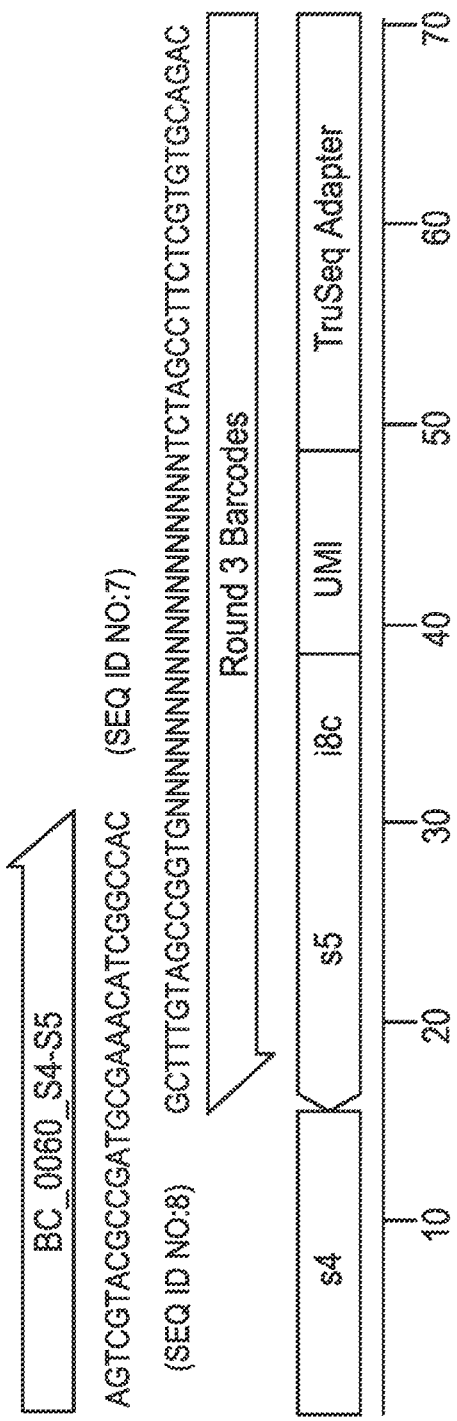
FIG. 13 depicts an annealed, third-round barcode oligo, according to an embodiment of the present disclosure.

FIG. 13 depicts an annealed, third-round barcode oligo. 96 third-round barcode oligos with unique sequences in domain i8c were used. In the third round, the unique sequence in domain i8c is the region of the sequence that is used as a barcode. By varying 8 nucleotides, there are 65,536 possible unique sequences. In some embodiments, more than 8 nucleotides may be present in domain i8c. In some other embodiments, less than 8 nucleotides may be present in domain i8c. The third round of barcodes can be preannealed to a linker strand (BC_0060) through complementary sequences in domain s5. The linker strand can include complementary sequence to part of the second-round barcode oligo (domain s4) that can allow it to hybridize and bring the 3' end of the second-round barcodes in close proximity to the 5' end of the third-round barcode oligo. The phosphate of the second-round barcode oligo can then be ligated to the 3' end of the third-round barcodes by T4 DNA ligase. The third-round barcode oligos can be synthesized with unique molecular identifiers (UMI; see Islam, et. al. Nature Methods, 2014) consisting of 10 random nucleotides (domain UMI: NNNNNNNNNN). Due to PCR amplification bias, multiple sequencing reads can originate from the cDNA. Using a UMI, each cDNA may be counted only once. The third-round barcodes can also include a domain corresponding to part of the ILLUMINA® TruSeq adapter. The third-round barcodes can be synthesized with a biotin molecule at the 5' end so that fully barcoded cDNA can be isolated with streptavidin coated magnetic beads.

Starting from a 100 μM stock of each barcode oligo (i.e., in 96-well plates, one for each round), 11 μl of barcode oligo were transferred to 96-well PCR plates. To the plate with the round 1 barcodes, 9 μl of BC_0056 (100 μM stock) were added to each well. To the plate with the round 2 barcodes, 9 μl of BC_0058 (100 μM stock) were added to each well. To the plate with the round 3 barcodes, 9 μl of BC_0060 (100 μM stock) were added to each well. Each plate was then placed in a thermocycler, with the following program, to anneal the barcodes with the corresponding linker oligo: heat to 90° C., reduce heat 0.1° C./second, and stop when the temperature reaches 25° C. 2.2 μl were transferred from each well having the round 1 barcodes into a new 96-well plate (referred to as plate L1). 3.8 μl were transferred from each well with the round 2 barcodes into a new 96-well plate (referred to as plate L2). 6.1 μl were transferred from each well with the round 3 barcodes into a new 96-well plate (referred to as plate L3).

Example 3—Preparation of Ligation Stop Oligos

Figure 14:
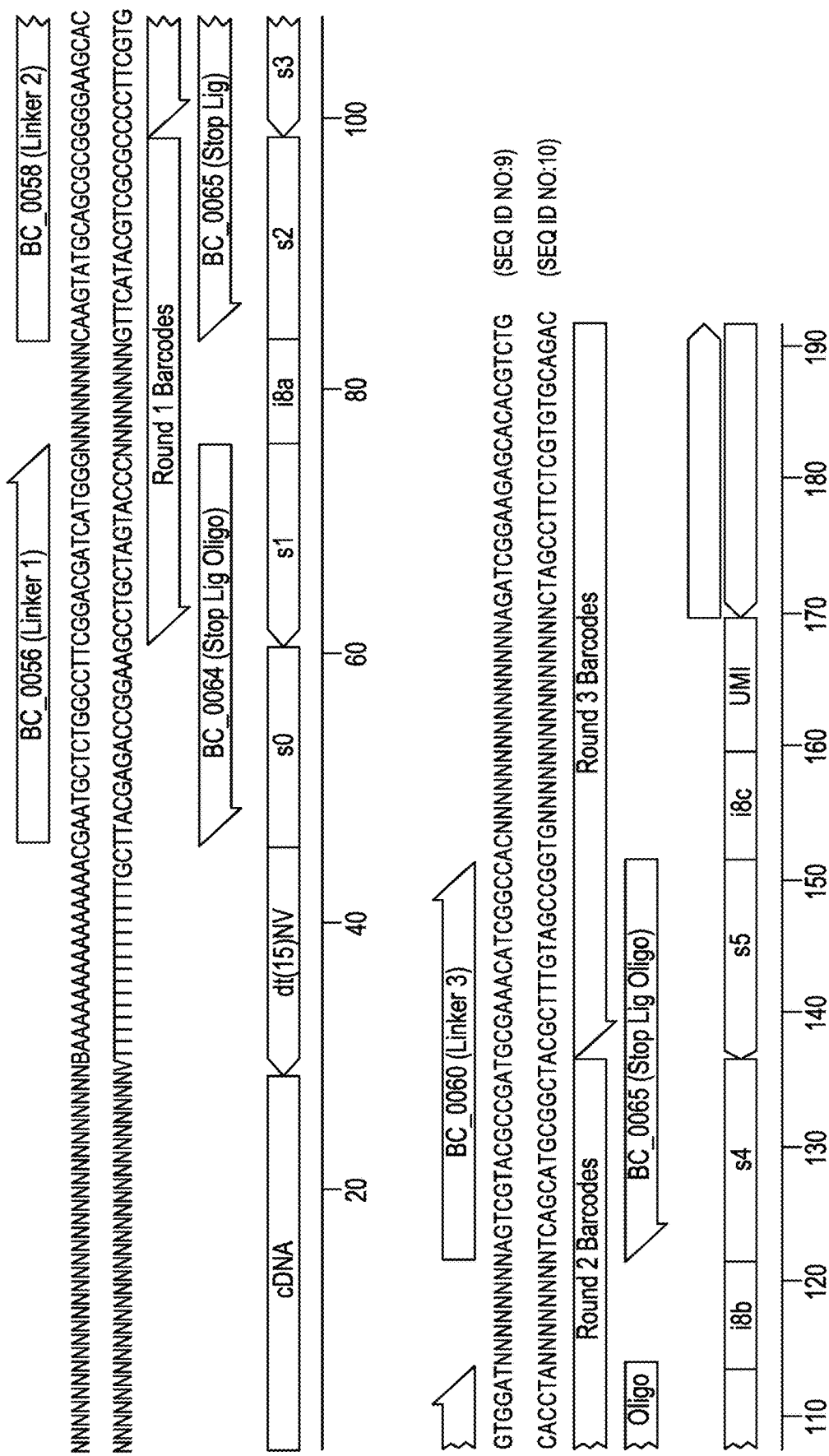
FIG. 14 depicts ligation stop oligos, according to an embodiment of the present disclosure.

After each round of ligation, the ligation can be stopped by adding an excess of oligo that is complementary to the linker strands (see FIG. 14). To stop each barcode ligation, oligo strands that are fully complementary to the linker oligos can be added. These oligos can bind the linker strands attached to unligated barcodes and displace the unligated barcodes through a strand displacement reaction. The unligated barcodes can then be completely single-stranded. As T4 DNA ligase is unable to ligate single-stranded DNA to other single-stranded DNA, the ligation reaction will stop progressing. To ensure that all linker oligos are bound by the complementary oligos, a molar excess of the complementary oligos (relative to the linker oligos) is added. To stop the first-round ligation, BC_0064 (complementary to BC_0056) is added. To stop the second-round ligation, BC_0065 (complementary to BC_0058) is added. To stop the third-round ligation, BC_0066 (complementary to BC_0060) is added.

Dilutions can be prepared for each stop ligation strand (BC_0064, BC_0065, BC_0066) as follows: 264 μl stop ligation strand (BC_0064, BC_0065, BC_0066), 300 μl 10× T4 DNA Ligase Buffer, and 636 μl nuclease-free water.

Example 4—Ligation of Barcodes to cDNA

5 μl 10% TRITON™ X-100 can be added to the reverse transcription reaction (to a final concentration of 0.1%) in the above-described 24-well plate. The reverse transcription (RT) reaction with cells can be transferred to a 15 ml conical centrifuge tube (FALCON™). The RT reactions can be spun for 10 minutes at 500× g and resuspended in 2 ml nuclease-free water. The cells can be combined with ligase mix (600 μl 10× T4 ligase buffer, 2040 μl of nuclease-free water, all of the resuspended cells (2000 μl), 100 μl of T4 DNA Ligase (NEW ENGLAND BIOLABS®, 400,000 units/ml), and 60 μl of 10% TRITON™ X-100) in a disposable pipetting reservoir (10 ml)). The cells and ligase mix can be mixed by gently tilting the reservoir back and forth several times. Using a multichannel pipette, 40 μl of the cells in the ligase mix can be added to each well of annealed round 1 barcodes (plate L1). Each well can be mixed by pipetting up and down gently 2-3 times. The cells in the ligase mix can be incubated at 37° C. for 60 minutes.

10 µl of the diluted BC_0064 can be added to each well to stop the ligation. The samples can then be incubated at 37° C. for 30 minutes. All of the cells can be collected in a new disposable pipetting reservoir (10 ml). The cells can be passed through a 40 µM strainer into a new disposable pipetting reservoir (10 ml) using a 1 ml pipette. 100 µl of T4 DNA ligase (NEW ENGLAND BIOLABS®, 400,000 units/ml) can be added to the cells in reservoir. The cells and ligase mix can be mixed by gently tilting the reservoir back and forth several times and using a multichannel pipette, 40 µl of the cells in the ligase mix can be added to each well of annealed round 2 barcodes (plate L2). Each well can be mixed by pipetting up and down gently 2-3 times and the samples can then be incubated at 37° C. for 60 minutes.

10 µl of the diluted BC_0065 can be added to each well to stop the ligation. The samples can be incubated at 37° C. for 30 minutes and the cells can then be collected in a new disposable pipetting reservoir (10 ml). The cells can be passed through a 40 µM strainer into a new disposable pipetting reservoir (10 ml) using a 1 ml pipette. 100 µl of T4 DNA ligase (NEW ENGLAND BIOLABS®, 400,000 units/ml) can be added to the cells in the reservoir. The cells and ligase mix can be mixed by gently tilting the reservoir back and forth several times. Using a multichannel pipette, 40 µl of the cells in the ligase mix can be added to each well of annealed round 3 barcodes (plate L3). Each well can then be mixed by pipetting up and down gently 2-3 times and the samples can be incubated at 37° C. for 60 minutes.

10 µl of the diluted BC_0066 can be added to each well to stop the ligation. The samples can be incubated at 37° C. for 30 minutes. All the cells can be collected in a new disposable pipetting reservoir (10 ml). The cells can be transferred to a 15 ml conical centrifuge tube (FALCON™) and the tube can be filled with wash buffer (nuclease-free water, 0.05% Tween 20, and 25% formamide) to 15 ml. The samples can be incubated for 15 minutes at room temperature. The cells can then be pelleted at 500× g for 10 minutes and the liquid can be removed without disturbing the pellet. Each tube of cells can be resuspended in 100 µl PBS and the cells can be counted (e.g., on a hemocytometer or on a flow cytometer). In one example, 57,000 cells were retained. The number of cells to be sequenced can be chosen. In one example, the cells were split into 25 cell, 250 cell, 2,500 cell, and 25,000 cell aliquots. 300 µl of lysis buffer (10 mM NaF, 1 mM $Na_3VO_4$, 0.5% DOC buffer, and 0.5% TRITON™ X-100) can be added to each of the cell aliquots and each of the cell aliquots can be passed through a 25 gauge needle eight times.

Example 5—Binding Barcoded cDNA to Streptavidin Coated Beads

First, DYNABEADS® MYONE™ Streptavidin C1 beads can be resuspended. 20 µl of resuspended DYNABEADS® MYONE™ Streptavidin C1 beads (for each aliquot of cells) can be added to a 1.7 ml microcentrifuge tube (EPPENDORF®). The beads can be washed 3 times with 1× phosphate buffered saline Tween 20 (PBST) and resuspended in 20 µl PBST. 900 µl PBST can be added to the cell aliquot and 20 µl of washed C1 beads can be added to the aliquot of lysed cells. The samples can be placed on a gentle roller for 15 minutes at room temperature and then washed 3 times with 800 µl PBST using a magnetic tube rack (EPPENDORF®). The beads can then be resuspended in 100 µl PBS.

Example 6—RNase Treatment of Beads

A microcentrifuge tube (EPPENDORF®) comprising a sample can be placed against a magnetic tube rack (EPPENDORF®) for 2 minutes and then the liquid can be aspirated. The beads can be resuspended in an RNase reaction (3 µl RNase Mix (ROCHE™), 1 µl RNase H (NEW ENGLAND BIOLABS®), 5 µl RNase H 10× Buffer (NEW ENGLAND BIOLABS®), and 41 µl nuclease-free water). The sample can be incubated at 37° C. for 1 hour, removed from 37° C., and placed against a magnetic tube rack (EPPENDORF®) for 2 minutes. The sample can be washed with 750 µl of nuclease-free water +0.01% Tween 20 ($H_2O$-T), without resuspending the beads and keeping the tube disposed against the magnetic tube rack. The liquid can then be aspirated. The sample can be washed with 750 µl $H_2O$-T without resuspending the beads and while keeping the tube disposed against the magnetic tube rack. Next, the liquid can be aspirated while keeping the tube disposed against the magnetic tube rack. The tube can then be removed from the magnetic tube rack and the sample can be resuspended in 40 µl of nuclease-free water.

Example 7-3' Adapter Ligation

Figure 15:
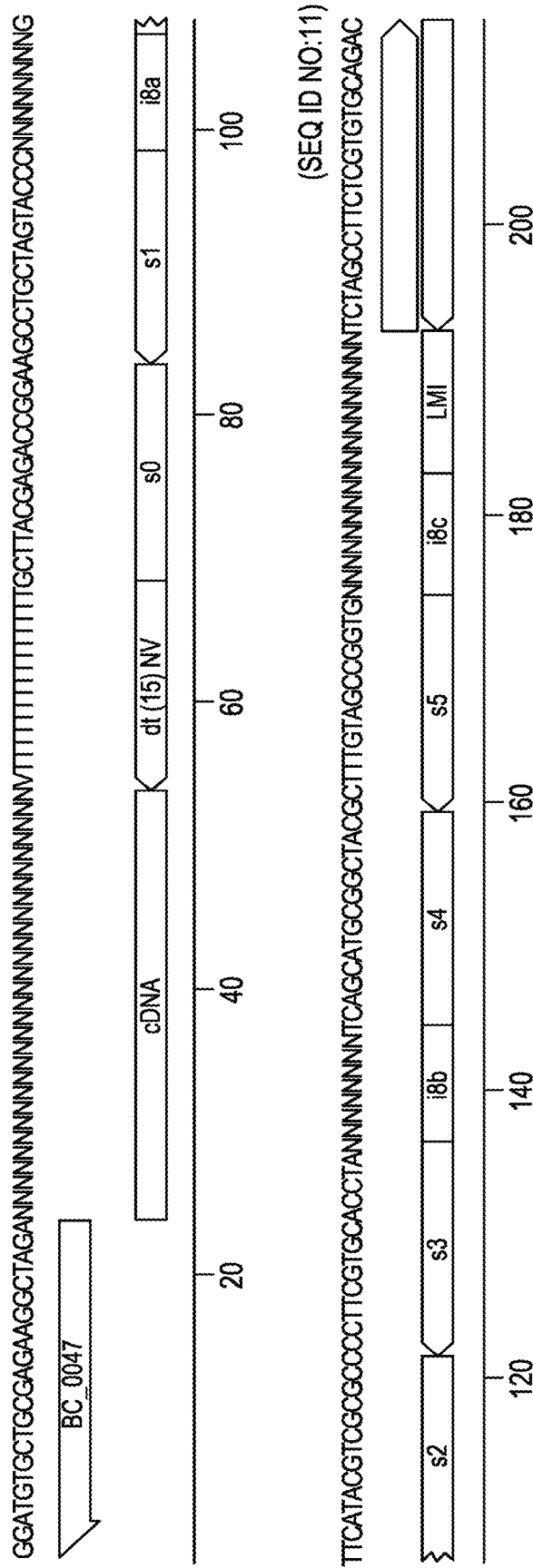
FIG. 15 depicts a single-stranded DNA adapter oligo (BC_0047) ligated to the 3' end of a cDNA, according to an embodiment of the present disclosure.

With reference to FIG. 15, to facilitate PCR amplification, a single-stranded DNA adapter oligo (BC_0047) can be ligated to the 3' end of cDNA. To prevent concatemers of the adapter oligo, dideoxycytidine (ddC) can be included at the 3' end of the adapter oligo. BC_0047 was generated with a phosphate at the 5' end and ddC at the 3' end. Several enzymes are capable of ligating single-stranded oligo to the 3' end of single-stranded DNA. Herein, T4 RNA ligase 1 (NEW ENGLAND BIOLABS®) was used. Thermostable 5' AppDNA/RNA Ligase (NEW ENGLAND BIOLABS®) can also be used with a preadenylated adaptor oligo.

Specifically, 20 µl of the RNase-treated beads can be added to a single PCR tube. 80 µl of ligase mix (5 µl T4 RNA Ligase 1 (NEW ENGLAND BIOLABS®), 10 µl 10× T4 RNA ligase buffer, 5 µl BC_0047 oligo at 50 µM, 50 µl 50% PEG 8000, and 10 µl 10 mM ATP) can be added to the 20 µl of the ligase mixed with the beads in the PCR tube. 50 µl of the ligase mixed with the beads can be transferred into a new PCR tube to prevent too many beads from settling to the bottom of a single tube and the sample can be incubated at 25° C. for 16 hours.

Example 8—Generating ILLUMINA® Compatible Sequencing Products

Figure 16:
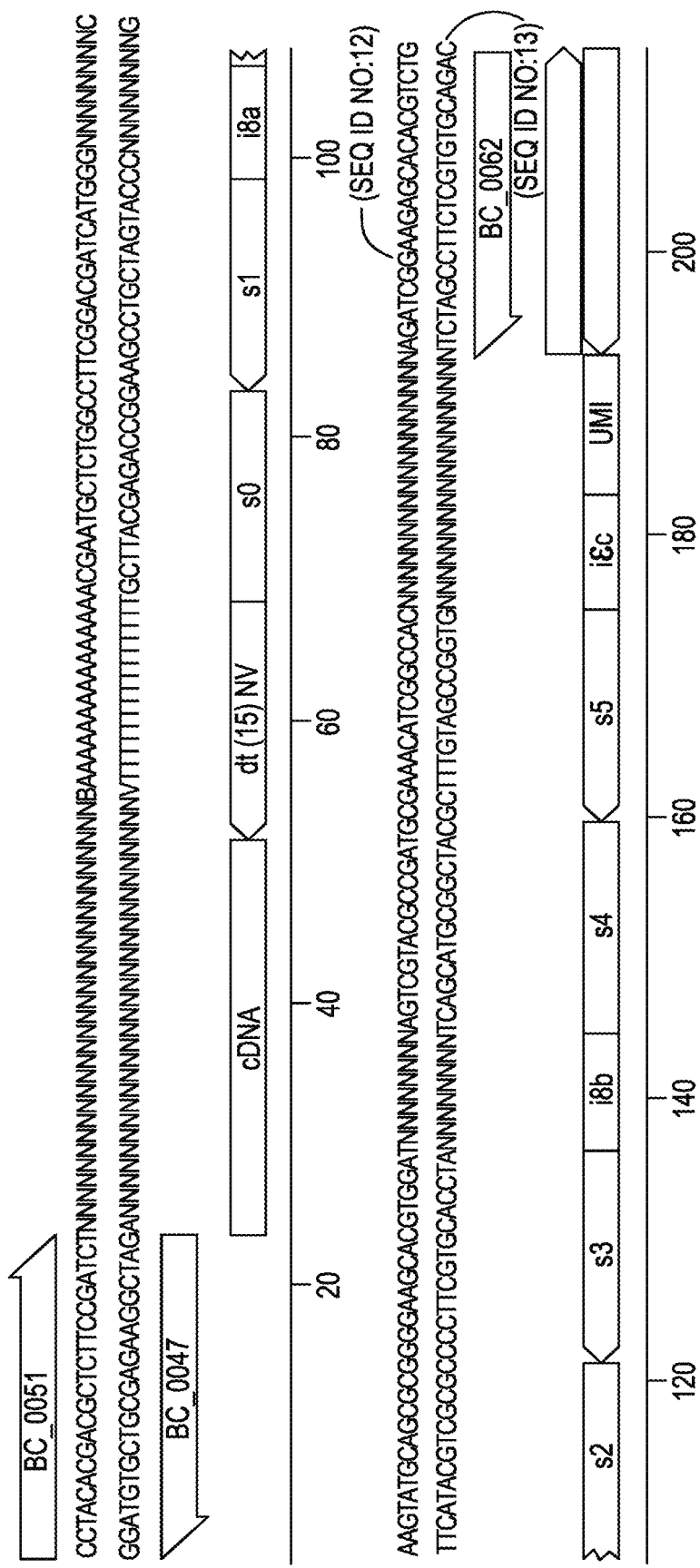
FIG. 16 depicts a PCR product formed using primers BC_0051 and BC_0062 and the 3' adapter oligo (BC_0047) after it has been ligated to barcoded cDNA.

Ligation reactions from both PCR tubes can be combined into a single 1.7 ml microcentrifuge tube (EPPENDORF®). 750 µl of $H_2O$-T can be added to each sample. Each of the tubes can be placed on a magnetic tube rack (EPPENDORF®) for 2 minutes, the liquid can be aspirated, and the samples can be resuspended in 40 µl water. The samples can be transferred to PCR tubes. 60 µl of PCR mix can be added to each tube (50 µl 2× PHUSION® DNA Polymerase Master Mix (THERMO FISHER™ Scientific), 5 µl BC_0051 (10 µM), and 5 µl BC_0062 (10 µM)). 10 cycles of PCR can be run (98° C. for 3 minutes, repeat 10 times (98° C. for 10 seconds, 65° C. for 15 seconds, and 72° C. for 60 seconds), and 72° C. for 5 minutes). FIG. 16 depicts the PCR product. After the 3' adapter oligo (BC_0047) has been ligated to barcoded cDNA, the cDNA can be amplified using PCR. As shown in FIG. 16, the primers BC_0051 and BC_0062 were used.

The PCR samples from the previous step can be procured and the magnetic beads can be displaced to the bottom of each tube with a magnet. 90 µl of PCR reaction can be transferred to a new 1.7 ml without transferring any of the magnetic beads. 10 µl of nuclease-free water can be added to each of the 1.7 ml tubes to a total volume of 100 µl. 60 µl of AMPURE™ beads can be added to the 100 µl of PCR reaction (0.6×SPRI) and bound for 5 minutes. The tubes can be placed against a magnet for 2 minutes and the samples can be washed with 200 µl of 70% ethanol (30 second wait) without resuspending the beads. The samples can be washed again with 200 µl of 70% ethanol (30 second wait) without resuspending the beads and then the samples can be air dried for 5-10 minutes until the ethanol has evaporated.

Each of the samples can be resuspended in 40 µl of nuclease-free water. The tubes can be placed against a magnetic rack for 2 minutes. While the microcentrifuge tubes (EPPENDORF®) are still disposed against the magnetic rack, 38 µl of solution can be transferred to a new 1.7 ml tube, without transferring beads. 62 µl of nuclease-free water can be added to the samples to a total volume of 100 µl. 60 µl of AMPURE™ beads can then be added to 100 µl of the PCR reaction (0.6×SPRI) and bound for 5 minutes. The tubes can be placed against a magnet for 2 minutes and then the samples can be washed with 200 µl of 70% ethanol (30 second wait) without resuspending the beads. The samples can be washed again with 200 µl 70% ethanol (30 second wait) without resuspending the beads and then the samples can be air dried for 5-10 minutes until the ethanol has evaporated.

Figure 17:
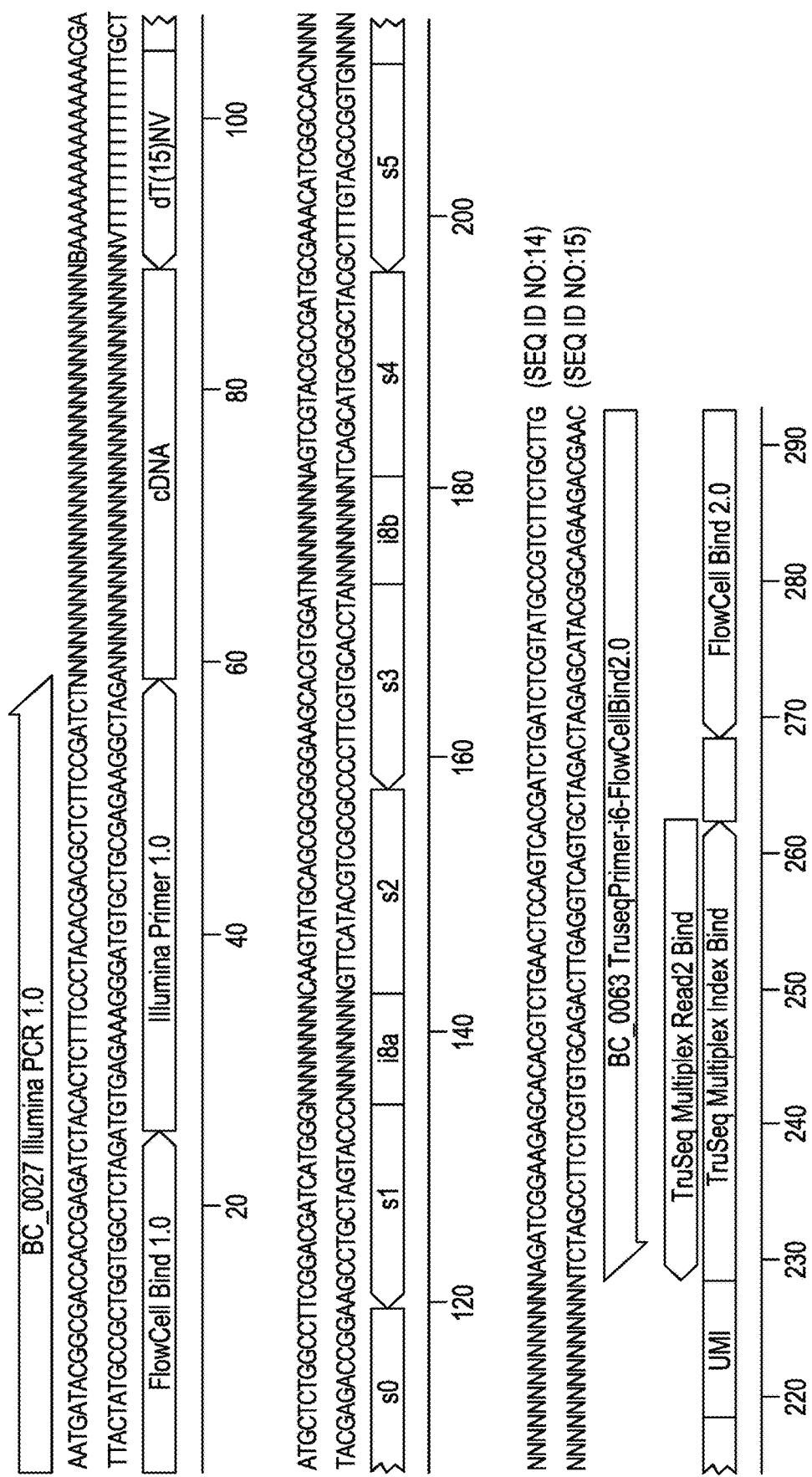
FIG. 17 depicts BC_0027, which includes the flow cell binding sequence and the binding site for the TRUSEQ™ read 1 primer and BC_0063, which includes the flow cell binding sequence and the TruSeq multiplex read 2 and index binding sequence.

The samples can be resuspended in 40 µl of nuclease-free water and each tube can be placed against a magnetic rack for 2 minutes. While the tube is still disposed against the magnetic rack, 38 µl of solution to a new 1.7 ml tube, without transferring any beads. 20 µl of the 38 µl elution can be added to an optical PCR tube. Furthermore, a PCR mix can be added to the tube (25 µl PHUSION® DNA Polymerase Master Mix (THERMO FISHER™ Scientific), 2.5 µl BC_0027 (10 µM), 2.5 µl BC_0063 (10 µM), and 2.5 µl 20× EVAGREEN® (Biotium)). Following the PCR depicted in FIG. 16, the full ILLUMINA® adapter sequences can be introduced through another round of PCR. As depicted in FIG. 17, BC_0027 includes the flow cell binding sequence and the binding site for the TRUSEQ™ read 1 primer. BC_0063 includes the flow cell binding sequence and the TruSeq multiplex read 2 and index binding sequence. There is also a region for the sample index, which is GATCTG in this example.

The above samples can be run on a qPCR machine with the following cycling conditions: 1) 98° C. for 3 minutes, 2) 98° C. for 10 seconds, 3) 65° C. for 15 seconds, 4) 72° C. for 60 seconds, and 5) repeat steps 2-4 (e.g., 10-40 times, depending on when fluorescence stops increasing exponentially). The tube can be transferred to a thermocycler set to 72° C. for 5 minutes. The qPCR reaction can be run on a 1.5% agarose gel for 40 minutes and a 450-550 bp band can be cut and gel extracted (QIAQUICK® Gel Extraction Kit). The products can be sequenced on an ILLUMINA® MISEQ™ using paired end sequencing. The sequencing primers can be the standard TRUSEQ™ multiplex primers. Read 1 can sequence the cDNA sequence, while read 2 can cover the unique molecular identifier as well as the 3 barcode sequences (8 nucleotides each). Index read 1 can be used to sequence sample barcodes, so multiple samples may be sequenced together.

Example 9—Data Analysis

Figure 18:
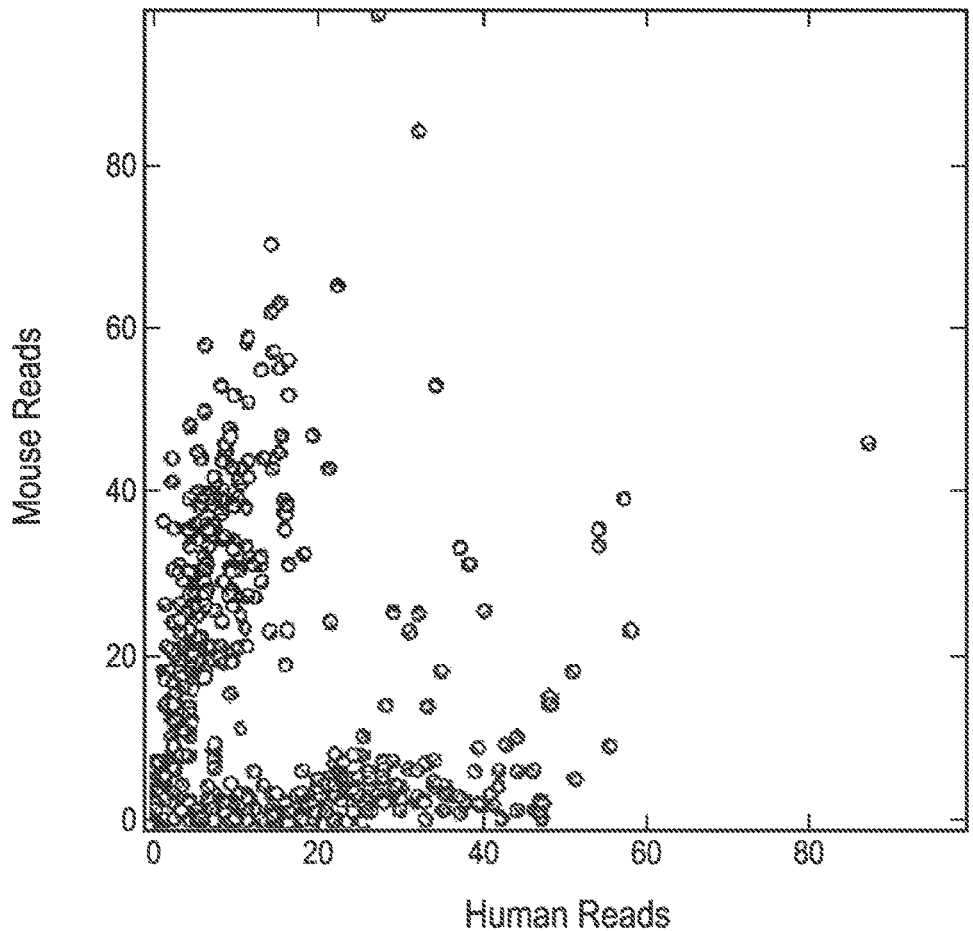
FIG. 18 is a scatter plot, wherein for each unique barcode combination the number of reads aligning to the human genome (x-axis) and the mouse genome (y-axis) are plotted.

Sequencing reads were grouped by cell barcodes (three barcodes of eight nucleotides each, 96×96×96=884,736 total combinations). Each barcode combination should correspond to the cDNA from a single cell. Only reads with valid barcodes were retained. The sequencing reads with each barcode combination were aligned to both the human genome and the mouse genome. Reads aligning to both genomes were discarded. Multiple reads with the same unique molecular identifier were counted as a single read. Reads with unique molecular identifiers with two or less mismatches were assumed to be generated by sequencing errors and were counted as a single read. For each unique barcode combination the number of reads aligning to the human genome (x-axis) and the mouse genome (y-axis) were plotted (see FIG. 18). As each cell is either mouse or human, it should ideally include only one type of RNA. So an ideal plot would have every point along the x- or y-axis. The fact that most points in the plot of FIG. 18 are near an axis indicates that the method is viable.

Each point in the plot corresponds to cDNA with the same combination of barcodes and should represent the cDNA from a single cell. For each point, the number of reads that map uniquely to the mouse genome are plotted on the y-axis, while the number of reads that map uniquely to the human genome are plotted on the x-axis. If cDNAs with a specific combination of barcodes came from a single cell, all of the cDNA with the specific combination of barcodes should map completely to the human genome or completely to the mouse genome. As stated above, the fact that most barcode combinations map close to either the x-axis (human cells) or the y-axis (mouse cells) indicates that the method can indeed produce single-cell RNA sequencing data.

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

The invention claimed is:

1. A method of labeling genomic DNA with cell-specific tags, the method comprising:
  (a) fixing and permeabilizing a plurality of cells;
  (b) generating a plurality of tagged genomic DNA fragments within each of the plurality of fixed and permeabilized cells,
    wherein each of the tagged genomic DNA fragments comprises an adapter sequence appended to one or both ends;
    wherein the plurality of fixed and permeabilized cells are present within a plurality of aliquots during the generating, with each aliquot comprising more than one cell; and
    wherein each of the plurality of tagged genomic DNA fragments comprises one or more aliquot-specific barcode sequences;
  (c) lysing the plurality of cells, thereby releasing the plurality of tagged genomic DNA fragments from each of the plurality of cells;
  (d) isolating the tagged genomic DNA fragments released from each of the plurality of cells;
  (e) amplifying the isolated tagged genomic DNA fragments using a plurality of amplification primers,
    wherein at least a portion of the plurality of amplification primers comprise an index sequence; and
    wherein multiple index sequences are present among the plurality of amplification primers; and
  (f) sequencing the amplified tagged genomic DNA fragments.

2. The method of claim 1, wherein the plurality of cells are fixed with formaldehyde.

3. The method of claim 1, wherein generating the plurality of tagged genomic DNA fragments in step (b) comprises fragmenting the genomic DNA within each of the plurality of fixed and permeabilized cells using a transposase, a restriction enzyme, and/or a DNase.

4. The method of claim 1, wherein generating the plurality of tagged genomic DNA fragments in step (b) comprises generating a plurality of genomic DNA fragments within each of the plurality of fixed and permeabilized cells, and appending an adapter sequence to the ends of the plurality of genomic DNA fragments using a ligase.

5. The method of claim 1, wherein generating the plurality of tagged genomic DNA fragments in step (b) comprises generating a plurality of adapter-tagged genomic DNA fragments within each of the plurality of fixed and permeabilized cells, and ligating nucleic acid tags comprising the one or more aliquot-specific barcode sequences to the adapter-tagged genomic DNA fragments.

6. The method of claim 5, wherein the nucleic acid tags are ligated to the adapter-tagged genomic DNA fragments prior to lysing the plurality of cells in step (c).

7. The method of claim 5, wherein the nucleic acid tags are ligated to the adapter-tagged genomic DNA fragments subsequent to lysing the plurality of cells in step (c).

8. The method of claim 1, wherein the plurality of cells are lysed using a protease.

9. The method of claim 8, wherein the protease is proteinase K.

10. The method of claim 1, wherein the released tagged genomic DNA fragments are isolated in step (d) using a binding agent.

11. The method of claim 10, wherein the binding agent comprises streptavidin beads.

12. The method of claim 1, wherein the sequencing of step (f) is performed using next-generation sequencing (NGS).

13. The method of claim 1, wherein the sequencing of step (f) comprises sequencing the one or more aliquot-specific barcode sequences.

14. The method of claim 1, wherein the isolated tagged genomic DNA fragments are present within a plurality of samples during the amplifying of step (e), and wherein the index sequences present among the amplification primers are sample-specific.

15. The method of claim 14, wherein the sequencing of step (f) comprises sequencing the sample-specific index sequences present introduced into the amplified tagged genomic DNA fragments by the amplification primers.

16. The method of claim 15, wherein the sequencing of step (f) comprises sequencing the one or more aliquot-specific barcode sequences and the sample-specific index sequences.

17. The method of claim 1, wherein the plurality of cells comprises at least 2,500, 25,000, or 50,000 cells.

18. The method of claim 1, further comprising mapping the sequencing reads generated in step (f) to a reference genome.

19. The method of claim 16, further comprising grouping the sequencing reads generated in step (f) using the one or more aliquot-specific barcode sequences and/or the sample-specific index sequences.

20. The method of claim 16, further comprising using the one or more aliquot-specific barcode sequences and/or the sample-specific index sequences to help determine the cell origin of each of the plurality of tagged genomic DNA fragments.

21. The method of claim 1, wherein the plurality of cells comprise mammalian cells.

22. The method of claim 1, wherein the plurality of aliquots are distributed into the wells of a multi-well plate.

23. The method of claim 22, wherein the multi-well plate is a 96-well plate.

* * * * *